(12) United States Patent
Mody et al.

(10) Patent No.: US 11,540,875 B2
(45) Date of Patent: Jan. 3, 2023

(54) MINIMALLY INVASIVE ACCESS CHANNELS INTO BODILY REGIONS

(71) Applicant: MicroCube, LLC, Fremont, CA (US)

(72) Inventors: Dinesh I. Mody, San Jose, CA (US);
Ketan Shroff, Pleasanton, CA (US);
Amrish J. Walke, Milpitas, CA (US);
Clarence Emmons, Capitola, CA (US);
Grason Ott, Fremont, CA (US);
Michael Dobrowski, San Francisco,
CA (US); Meera Mody, San Jose, CA (US)

(73) Assignee: MicroCube, LLC, Fremont, CA (US)

( * ) Notice: Subject to any disclaimer, the term of this patent is extended or adjusted under 35 U.S.C. 154(b) by 606 days.

(21) Appl. No.: 14/801,754

(22) Filed: Jul. 16, 2015

(65) Prior Publication Data
US 2016/0015259 A1 Jan. 21, 2016

Related U.S. Application Data

(60) Provisional application No. 62/025,359, filed on Jul. 16, 2014.

(51) Int. Cl.
*A61B 1/018* (2006.01)
*A61B 1/00* (2006.01)
(Continued)

(52) U.S. Cl.
CPC ...... *A61B 18/1492* (2013.01); *A61B 1/00078* (2013.01); *A61B 1/00135* (2013.01);
(Continued)

(58) Field of Classification Search
CPC ...... A61B 17/3415; A61B 2018/00559; A61B 2017/4216; A61B 17/42–442;
(Continued)

(56) References Cited

U.S. PATENT DOCUMENTS 4,846,153 A * 7/1989 Berci ................. A61B 1/00135
600/109
5,575,788 A * 11/1996 Baker ..................... A61N 1/056
606/41

(Continued)

*Primary Examiner* — Colin T. Sakamoto
(74) *Attorney, Agent, or Firm* — Levine Bagade Han LLP

(57) ABSTRACT

The present invention discloses access devices and methods to create an access channel for introduction of one or more working devices into an anatomical region. The access channel is created using a visualization modality that is later removed before inserting one or more working devices through the access channel. This allows the methods and devices of the present invention to be used even in small sized natural or surgically created insertion tracts leading to the anatomical region. The access channel can be made of a device such as a sheath, a guidewire, and an elongate device comprising a lumen. Examples of visualization modalities are endoscopes and body insertable ultrasound imaging devices. The working devices can be used to perform a variety of diagnostic, therapeutic, or preventive procedures. Endometrial ablation devices and procedures have been used as an example to describe various aspects of the present invention.

24 Claims, 24 Drawing Sheets

(51) Int. Cl.
*A61B 8/12* (2006.01)
*A61B 1/04* (2006.01)
*A61B 1/32* (2006.01)
*A61B 18/14* (2006.01)
*A61B 1/303* (2006.01)
*A61B 8/08* (2006.01)
*A61B 18/00* (2006.01)

(52) U.S. Cl.
CPC ............ *A61B 1/303* (2013.01); *A61B 8/0841* (2013.01); *A61B 8/12* (2013.01); *A61B 8/481* (2013.01); *A61B 2018/00559* (2013.01); *A61B 2018/00577* (2013.01); *A61B 2018/00982* (2013.01)

(58) Field of Classification Search
CPC ....... A61B 2017/4208–447; A61B 2017/3445; A61B 2017/22072–22078; A61B 2018/00982
See application file for complete search history.

(56) References Cited

U.S. PATENT DOCUMENTS

| | | | |
|---|---|---|---|
| 6,002,968 A * | 12/1999 | Edwards | A61B 18/1477 606/41 |
| 6,006,755 A * | 12/1999 | Edwards | A61B 18/148 606/41 |
| 6,743,184 B2 | 6/2004 | Sampson et al. | |
| 6,872,183 B2 | 3/2005 | Sampson et al. | |
| 7,736,360 B2 | 6/2010 | Mody et al. | |
| 8,968,287 B2 | 3/2015 | Shroff et al. | |
| 2008/0188850 A1 | 8/2008 | Mody et al. | |
| 2008/0245371 A1* | 10/2008 | Gruber | A61B 1/303 128/831 |
| 2009/0240198 A1* | 9/2009 | Averbuch | A61M 25/04 604/96.01 |
| 2009/0270812 A1 | 10/2009 | Litscher et al. | |
| 2010/0016784 A1 | 1/2010 | Mody et al. | |
| 2010/0087798 A1* | 4/2010 | Adams | A61B 1/303 604/515 |
| 2010/0121319 A1* | 5/2010 | Chu | A61B 18/18 606/33 |
| 2010/0125269 A1 | 5/2010 | Emmons et al. | |
| 2010/0137857 A1 | 6/2010 | Shroff et al. | |
| 2011/0004205 A1 | 1/2011 | Chu et al. | |
| 2011/0112432 A1 | 5/2011 | Toth | |
| 2011/0112523 A1 | 5/2011 | Toth et al. | |
| 2012/0116378 A1 | 5/2012 | Toth et al. | |
| 2013/0256302 A1 | 10/2013 | Chu et al. | |
| 2013/0296686 A1* | 11/2013 | Sarna | A61B 5/0084 600/407 |
| 2014/0005650 A1 | 1/2014 | Burnett et al. | |
| 2014/0012156 A1 | 1/2014 | Burnett et al. | |
| 2014/0190960 A9 | 7/2014 | Chu et al. | |
| 2014/0214020 A1 | 7/2014 | Vissay et al. | |
| 2015/0045780 A1 | 2/2015 | Burnett et al. | |

* cited by examiner

MINIMALLY INVASIVE ACCESS CHANNELS INTO BODILY REGIONS

CROSS-REFERENCE TO RELATED APPLICATION DATA

This application claims benefit of U.S. Provisional Application No. 62/025,359, filed Jul. 16, 2014, which is incorporated by reference herewith in its entirety.

BACKGROUND

Minimally invasive medical procedures often involve introducing working devices through natural or artificial tracts leading to a target anatomical region. The introduction of devices is often carried out using visualizing devices such as endoscopes or body insertable ultrasound imaging devices. Examples of such procedures are: 1. Laparoscopy procedures for the stomach, liver, or other abdominal organs, 2. Arthroscopy procedures for joints, 3. Bronchoscopy procedures for trachea and bronchi of the lungs, 4. Colonoscopy procedures for the entire length of the colon and large intestine, 5. Colposcopy and hysteroscopy procedures for vagina, cervix, and the uterine cavity, 6. Cystoscopy procedures for the bladder lumen, 7. Esophagoscopy procedures for the Esophagus 8. Gastroscopy procedures for the Stomach and duodenum, 9. Laryngoscopy procedures for the larynx 10. Neuroendoscopy procedures for areas of the brain, 11. Proctoscopy procedures for the rectum and sigmoid colon, 12. Sigmoidoscopy procedures for the sigmoid colon, and 13. Thoracoscopy procedures for the pleura covering the lungs and structures covering the heart.

In many situations, the insertion tract is too narrow for inserting a visualizing device and a working device together. For example, a natural opening leading to an organ may be too narrow. Surgically enlarging the natural opening might entail medical risks and might also increase the pain generated during the procedure. This is commonly encountered, for example, during transcervical procedures. Dilating the cervix to increase the cervical lumen size carries the risk of perforating the insertion tract. Also, dilating the cervix increases the pain during the procedure making several transcervical procedures too painful to be done in the office.

For similar reasons, artificially created surgical openings leading to target anatomical regions are kept as small as possible to reduce the invasiveness of the procedure. For example, laparoscopic openings are kept as small as possible to reduce the pain, scarring, and medical risks of laparoscopic procedures.

One option in such cases is to introduce the working device without visualization. However, this carries the risk that the device placement may not be perfect. In addition, there is the risk that the device may perforate the insertion tract or surrounding organs and be placed in an improper location.

Hence there is a need for access devices and methods that can be used even in small sized insertion tracts to create a stable access channel for introduction of one or more working devices into the anatomy.

SUMMARY

The present invention discloses access devices and methods to create an access channel for introduction of one or more working devices into an anatomical region. The access channel is created using a visualization modality that is later removed before inserting one or more working devices through the access channel. This allows the methods and devices of the present invention to be used even in small sized natural or surgically created insertion tracts leading to the anatomical region. Allowing procedures to be performed in small insertion tracts reduces the medical risks of a procedure e.g. the risk of perforating the insertion tract and also reduces the pain during the procedure potentially allowing procedures to be done in the office. Further, creating an access channel allows devices to be repeatedly introduced into the anatomy through the access channel without causing additional trauma to the anatomy or without needing to navigate the devices themselves through the anatomy.

Various aspects of the present invention have been described using the uterine cavity as an example of an anatomical region, endometrial ablation devices as examples of working devices, the uterocervical canal as an example of the insertion tract, and hysteroscopes and intra-uterine ultrasound probes as examples of the visualization modalities. But it should be noted that the present invention has applications in several other situations. For example, the present invention may be used to introduce one or more working devices in cavities or lumens including, are not limited to: natural or artificially created cavities or lumens in portions of the male urinary tract, gall bladder, uterus and other portions of the female reproductive tract, regions of the vasculature, intestine and other portions of the lower alimentary tract, stomach and other portions of the upper alimentary tract, liver and other digestive organs, lungs, skin, mucus membranes, kidneys, reproductive organs, or other organs or soft tissues of the body. The present invention may also be used to introduce one or more working devices in solid (non-cavity) anatomical regions or organs such as the liver and brain. Even though endometrial ablation devices have been used as an example in several embodiments herein, other procedures such as lesion removal, adhesion lysis, lumen occlusion, targeted biopsy, and injections, etc. can be performed using the devices and methods disclosed herein.

The access channel can be made of a device such as a sheath, a guidewire, and an elongate device comprising a lumen. Any of the access channels may comprise one or more steering mechanisms comprising one or more attachments or integral elements to enable the user to steer or navigate devices through the anatomy. Embodiments wherein the access channel is a sheath, the sheath can act as an endoscope sheath wherein a lumen or space between the endoscope and the sheath is used for introducing or withdrawing fluids to/from the anatomy. Various methods and devices for introducing and/or withdrawing fluids to/from the anatomy and distending an anatomical region are also disclosed in this specification.

Various method embodiments herein describe endoscopic examinations or monitoring performed before, during, or after a medical procedure. Various working device embodiments described herein comprise a working element that is converted from a low profile insertion configuration to a larger profile working configuration in the anatomical region. Various methods described herein involve the use of folding mechanisms to fold or otherwise convert a working element to a low profile insertion configuration.

Examples of visualization modalities are endoscopes and body insertable ultrasound imaging devices. The working devices can be used to perform a variety of diagnostic, therapeutic, or preventive procedures.

The devices and/or methods disclosed in the following commonly assigned applications and/or patents can be incorporated with the methods and devices disclosed herein:

U.S. Pat. No. 8,968,287 filed Oct. 21, 2009 issued Mar. 3, 2015; U.S. Publication No. US-2011-0004205-A1 filed Jul. 1, 2010 published Jan. 6, 2011; U.S. Publication No. US-2010-0121319-A1 filed Oct. 21, 2009 published May 13, 2010; and U.S. Publication No. US-2014-0190960-A9 filed Apr. 1, 2013 published Jul. 10, 2014. Where the entirety of each of these publications and/or patents are incorporated by reference herein.

DETAILED DESCRIPTION

This invention related to devices and methods for creating minimally invasive, low profile, access channels to an anatomical region. The low profile of the access channels and the flexible nature of the devices reduce the invasiveness of the procedure. The access channels may then be used to introduce and/or remove one or more devices and/or fluids into or from the bodily region to perform one or more medical procedures. One of the advantages of creating an access channel is that devices may be repeatedly introduced into the anatomy through the access channel without causing additional trauma to the anatomy or without needing to navigate the devices themselves through the anatomy. Another advantage is the accurate placement of the devices without needed additional guidance or imaging while placing the devices. Another advantage is increased patient comfort while placing the devices. The invention also discloses methods and devices for creating access channels and performing one or more procedures under endoscopic guidance.

In a significant portion of the disclosure, the present invention has been described using the uterus as an example of a target organ, a hysteroscope as an example of an endoscope and hysteroscopic methods as examples of endoscopic methods.

Figure 1A:
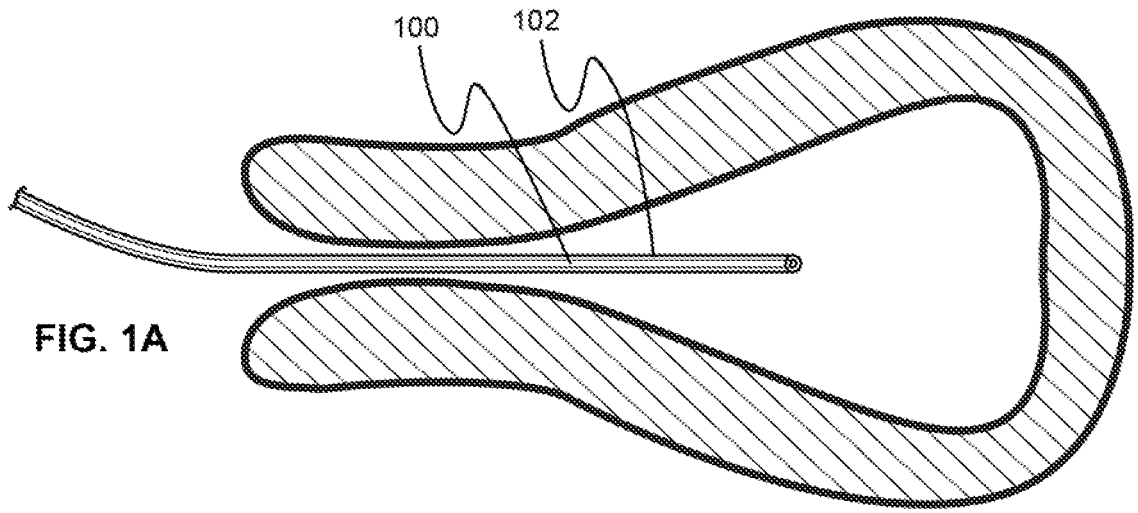
FIGS. 1A-1F show the steps of an embodiment of the method of performing a hysteroscopic procedure in the uterine cavity after creating a flexible, low profile access channel into the cavity.

FIGS. 1A-1F show the steps of an embodiment of the method of performing a hysteroscopic procedure in the uterine cavity after creating a flexible, low profile access channel into the cavity. In FIG. 1A, a hysteroscope 100 is introduced through a cannula 102 into the uterine cavity through the cervix. Cannula 102 acts as a sheath to endoscope 100 and also as a channel into the uterine cavity.

Figure 1B:
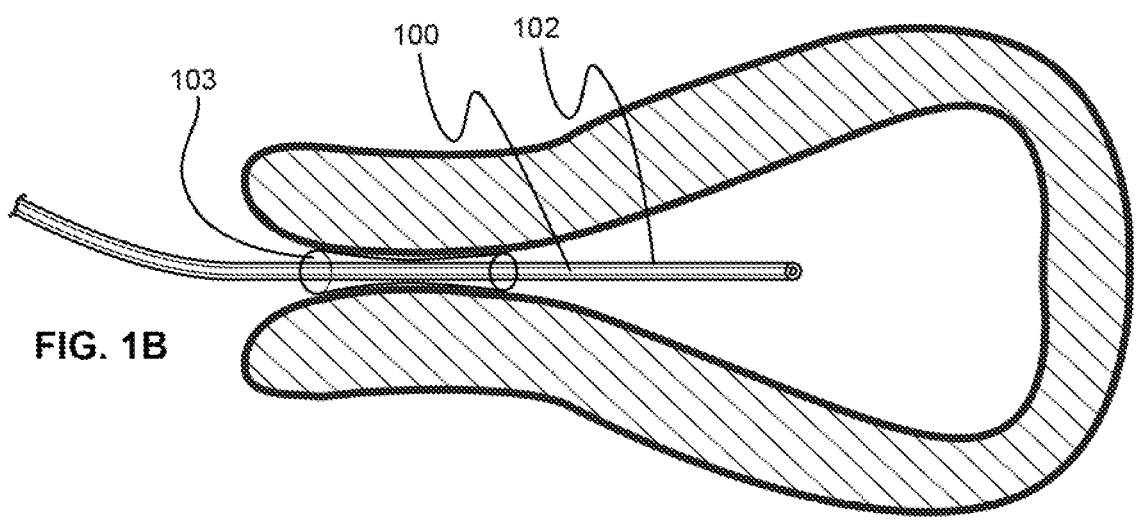
Figure 1C:
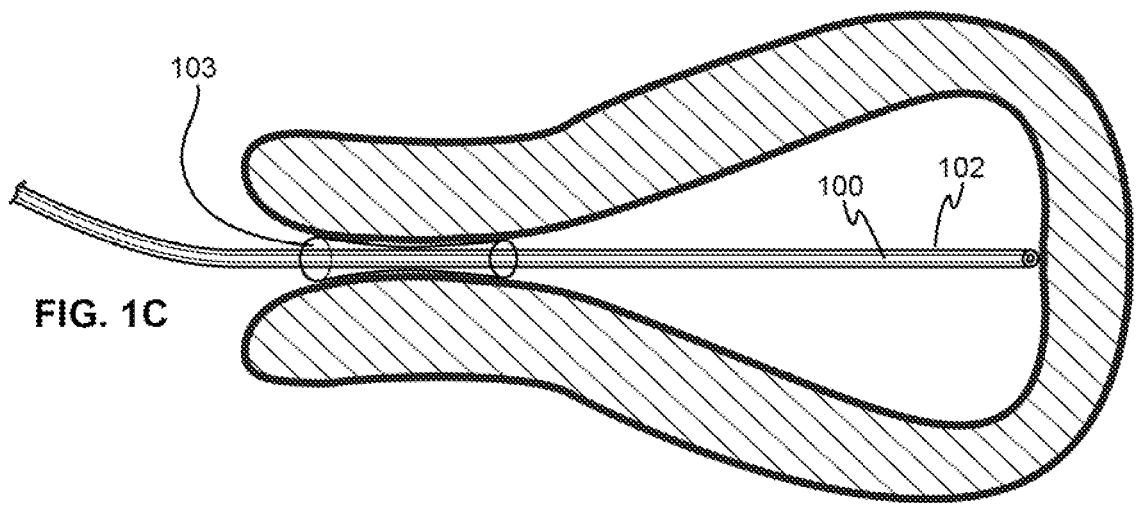

In FIGS. 1B and 1C, hysteroscope 100 is used to guide the navigation of cannula 102 through the uterine cavity such that the distal tip of the cannula 102 is positioned at the desired location within the uterine cavity. Examples of such locations include, but are not limited to: touching the fundus, adjacent to the fundus, adjacent or within a cornu, at the mid corpus region of the cavity, and adjacent or within the internal os. Also, in FIG. 1B, a plug 103 is deployed over cannula 102 between the outer surface of cannula 102 and the surrounding anatomy. Plug 103 may be deployed to create a complete or partial fluid seal between the outer surface of cannula 102 and the surrounding anatomy.

Figure 1D:
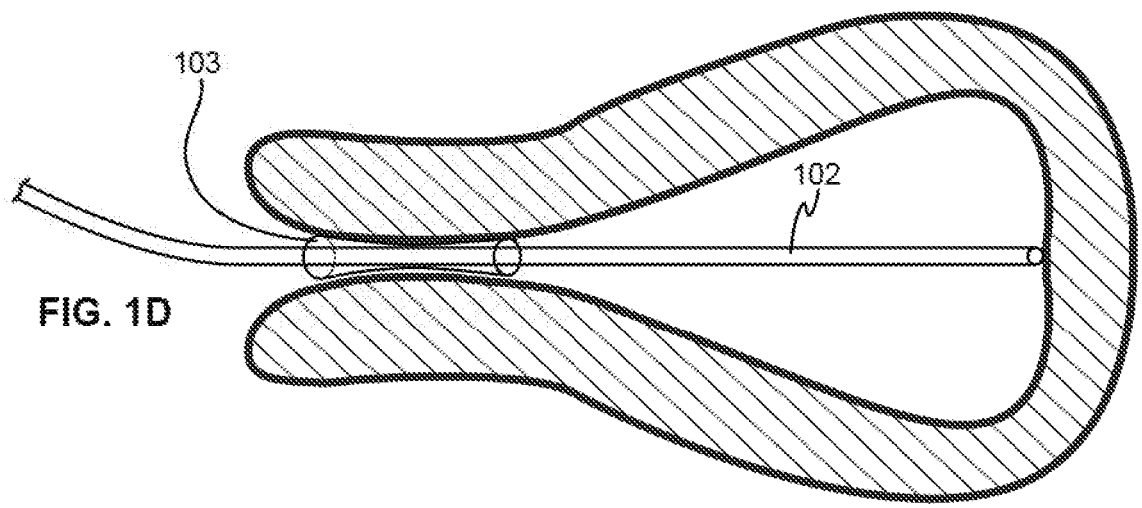

In FIG. 1D, the hysteroscope is removed leaving the cannula 102 positioned within the uterine cavity. In one embodiment, hysteroscope 100 is removed without dislodging or moving the position of cannula 102. This creates a pathway or access channel into the uterine cavity wherein the proximal end of the channel is present outside the patient's body and the distal end is positioned at the desired location within the uterine cavity for performing a procedure. The position of plug 103 may be adjusted if needed in any of the steps shown in FIGS. 1C-1F.

Figure 1E:
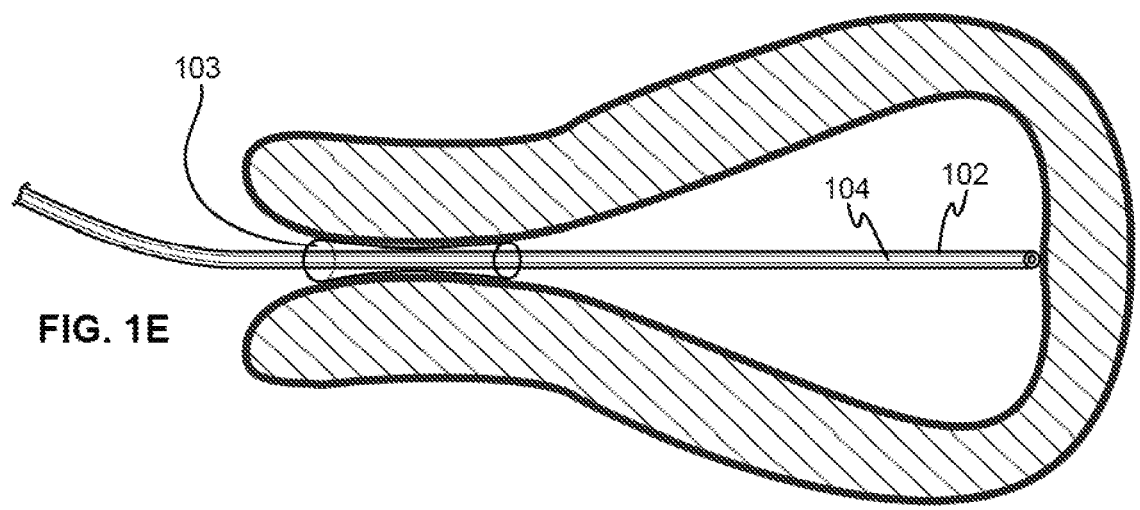

In FIG. 1E, a working device 104 is introduced through cannula 102 into the uterine cavity. Since the distal end of the cannula 102 is positioned at the desired location, the distal end of working device 104 will also emerge at the desired location. Examples of such locations include, but are not limited to: touching the fundus, adjacent to the fundus, adjacent or within a cornu, at the mid corpus region of the cavity, and adjacent or within the internal os.

Figure 1F:
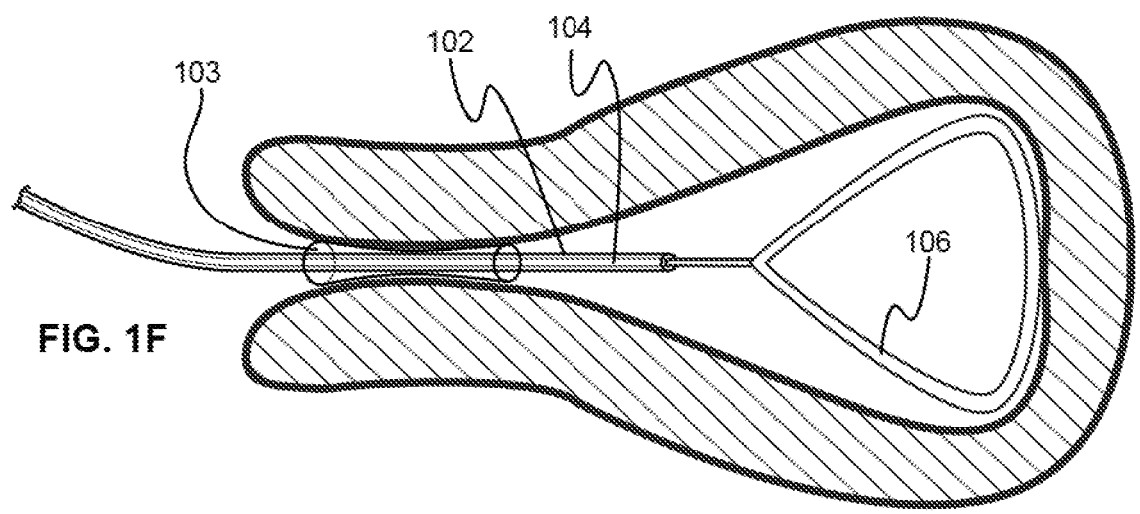

In FIG. 1F, working device 104 is deployed in the uterine cavity through cannula 102 to perform a diagnostic, therapeutic, or preventive procedure. In the embodiment shown, working device 104 is an endometrial ablation device comprising an antenna 106 and is used to perform an endometrial ablation procedure. In one alternate embodiment, in addition to the introduction of working device 104 through cannula 102, endoscope 100 is introduced between the outer surface of cannula 102 and the uterus into the uterine cavity.

In any of the embodiments herein, hysteroscope 100 may be used to perform one or more diagnostic examinations or procedures. In one embodiment, the hysteroscope is used to perform one or more qualitative examinations of the uterine cavity. Examples of such qualitative examinations include, but are not limited to:

1. Screening the uterine cavity or the uterus against inclusion and exclusion criteria for performing a procedure such as endometrial ablation, tubal occlusion, removal of a pathology, targeted biopsy, etc. More examples of such procedures include, but are not limited to:
   a. checking for pregnancy or conception products
   b. checking for cervical or uterine cancer or pre-malignant conditions of the endometrium, such as unresolved adenomatous hyperplasia.
   c. checking foractive genital or urinary tract infection
   d. checking for pelvic inflammatory disease.
   e. checking for anatomic or pathologic weakness or thinning of the myometrium. For example due to Cesarean section, myomectomy, etc.
   f. checking forabnormal, obstructed or perforated cavity. For example, checking for adhesions.
   g. checking for the presence of an intrauterine implant, such as intrauterine device (IUD).
   h. checking for abnormal uterine cavity shape.
   i. checking if the uterine cavity length is less than a certain cut off e.g. 4 cm.
2. checking the presence or absence of fluid in the uterine cavity
3. checking for the location and extent of C-section scars
4. checking for the presence of blood clots
5. checking the endometrial layer for pathology such as cancer, hyperplasia, thin or thick endometrium, etc.
6. checking the wall strength or structural strength of the uterine wall.
7. checking for perforations of the uterine wall.

In one such embodiment, the procedure of checking for perforation is performed after cavity distension. In another embodiment, the procedure comprises detecting visual clues e.g. holes in the uterine wall. In another embodiment, the procedure comprises detecting fluid flow in the uterine cavity. In another embodiment, the procedure comprises detecting bubbles generated or present in the uterine cavity. In another embodiment, the procedure comprises detecting the uterine cavity collapse in spite of distending the cavity under pressure.

If a perforation is detected, the hysteroscope may be used to insert a device that closes the perforation. Examples of such devices include, but are not limited to: devices for suturing the perforation, devices for deploying an occluding member into or around the perforation, devices for injecting glues (e.g. self curing glues, UV curing glues, etc) in or around the perforation, etc.

8. determining the shape and/or orientation of the uterine cavity, and
9. checking for false passages in the uterus.

In one embodiment, the hysteroscope is used to perform one or more quantitative examinations of the uterine cavity. Examples of such quantitative examinations include, but are not limited to:

1. Measuring the uterine cavity length (distance from the fundus to the internal os)
2. Measuring the sounding length (distance from the fundus to the external os)
3. Measuring the uterine cavity width
4. Measuring the endometrial thickness. This can be done, for example, by using a puncturing device that penetrates into the endometrium to measure the endometrial thickness by the penetration depth.

Any of the visualization methods herein may be used to determine and/or modify at least one treatment parameter (e.g. ablation power, ablation time, energy dose, deployed size of a working element, treatment temperature, treatment target, zone of resection, cutting site, etc.) of the medical procedure. For example, visualization may be used to set an energy dose for an ablation procedure such that larger anatomical regions get a larger dose and smaller anatomical regions get a smaller dose.

Hysteroscope 100 and working device 104 may be inserted into the uterine cavity by a variety of methods. In one embodiment, hysteroscope 100 and working device 104 are inserted together into the uterine cavity. In another embodiment, Hysteroscope 100 is inserted into and removed from the uterine cavity before working device 104 is inserted into the uterine cavity. In one embodiment, the distal end of hysteroscope 100 is located one of: proximal to, distal to or at the approximate mid-point of antenna 106. In one embodiment, hysteroscope 100 is positioned at the internal os during an ablation procedure. In another embodiment, hysteroscope 100 and working device 104 are integrated into a single device. The single device is then inserted into the uterine cavity using cannula 102.

Any of the access channels disclosed herein including cannula 102 may comprise one or more steering mechanisms comprising one or more attachments or integral elements to enable the user to steer or navigate cannula 102 through the anatomy. Examples of steering mechanisms include, but are not limited to: pull wires, pre-shaped tubular sheaths or stylet structures, expandable structures, balloons, surgical navigation elements, stiff and slidable elements, stiff and torqueable elements, and one or more elements adapted to be steered by a surgical magnetic navigation modality. Examples of such steerable systems are disclosed in U.S. Pat. No. 7,736,360, US Patent Publication No. 2008-0188850 and US Patent Publication No. 2010-0016784, the entire disclosures of which are incorporated herein by reference. Cannula 102 may comprise one or more handle portions or controls on or near the proximal end to control the movement of steering mechanisms and in turn the movement of cannula 102 from a proximal region portion. The movement of cannula 102 may occur in any three dimensional space.

Any of the access channels disclosed herein including cannula 102 may comprise one or more sealing mechanisms, examples of which are disclosed herein, to seal a region between cannula 102 and surrounding anatomy. The sealing mechanism may be integral to cannula 102 or may be a discrete device that cooperates with cannula 102. The sealing mechanism may be used to create a fluid tight seal.

Any of the access channels disclosed herein including cannula 102 may comprise one or more lumens or passages to enable the user to introduce and/or remove one or more fluids and devices through cannula 102. The lumens or passages may be rigid or flexible or collapsible.

Cannula 102 may be made of one or more biocompatible materials including, but not limited to: metals, polymers (including, but not limited to: PEBAX, Teflon, polyethylene, and polypropylene), glass, and ceramics. Portions of cannula 102 may be more flexible than other portions of cannula 102. In one such embodiment, a distal region of cannula 102 is more flexible than a proximal region of cannula 102.

An endoscopic examination may be performed during a therapy to monitor the performance, safety or effect of the therapy. In such an embodiment, the endoscope 100 and working device 104 are present in the anatomy at the same time. The endoscope 100 and working device 104 may be inserted in the anatomy through the same or different lumens of cannula 102. In one embodiment, a therapy procedure is performed under hysteroscopic visualization to monitor the performance, safety or effect of the therapy. This method may include one or more steps including, but not limited to: confirmation of antenna 106 deployment, monitoring the change in color of uterine walls, detecting steam generation, detecting charring, monitoring integrity of antenna 106 and other device components, deciding to terminate the procedure based on hysteroscopic feedback, determining the possibility of scar formation, detecting melting or breakage of device components, detecting sticking of one or more device components to tissue, measuring the temperature, monitoring the change in shape of a device component, monitoring the change in color of a thermochromic material, and determining the prognosis/outcome and follow-up based on hysteroscopic feedback.

An endoscopic examination may be performed after a therapy to confirm the performance, safety or effect of the therapy. In one such embodiment, a hysteroscopic examination may be performed after an endometrial ablation procedure to confirm one or more of: surface coverage of the lesion, presence of the lesion in regions such as the lower uterine region and the cornual regions, absence of the lesion from a C-section scar, and presence or absence of charring. If the lesion coverage is not satisfactory, the method further comprises the step of reinserting the ablation device 104 through cannula 102 or other access channels disclosed herein and re-treating the patient.

In any of the methods disclosed herein, the shape and/or the position and/or the orientation of the anatomy may be changed to facilitate a procedure. In one such embodiment, the uterine shape is modified. In another embodiment, the uterus is straightened (e.g. by grasping and pulling the cervix with a tenaculum) so that the uterine cavity is aligned with the cervical canal. In another embodiment, one or more regions of the uterus are displaced or moved to a desired location.

Figure 1G:
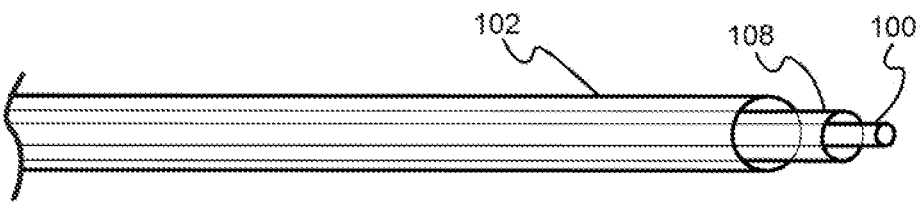
FIG. 1G shows an embodiment of an access channel loaded over an endoscope.

FIG. 1G shows an embodiment of an access channel loaded over an endoscope. In FIG. 1G, the access channel comprises a flexible cannula 102 and a stiffening member comprising a rigid or semi-rigid tube 108 located within a lumen of the cannula 102. The tube 108 is stiffer than cannula 102 and increases the stiffness of the assembly. This has the advantage of protecting a delicate endoscope by preventing the creation of sharp bends in the endoscope during use. Tube 108 encloses an endoscope 100. The combination of the access channel and the endoscope 100 comprises one or more lumen or channels between or within one or more of the constituent devices. The lumens or channels may be used for one or more of: flushing, distension, fluid evacuation, fluid circulation, and other steps disclosed herein. Any of the cannula 102 and tube 108 embodiments disclosed herein may be designed to reversibly lock to or otherwise grip endoscope 100 while creating a substantially fluid tight seal.

Figure 1H:
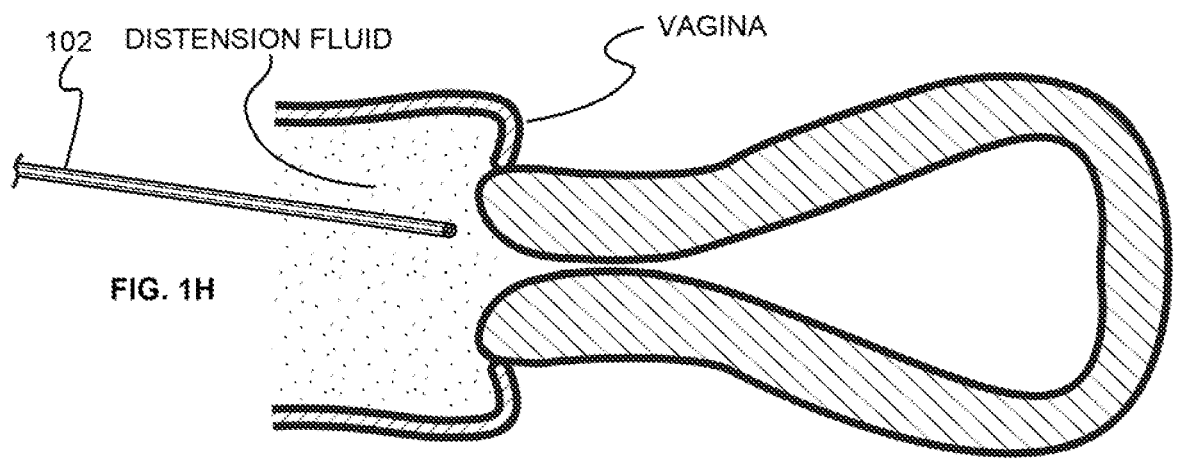
FIGS. 1H-1P show the steps of a method of treating a uterine cavity using the vaginoscopic technique.
Figure 1I:
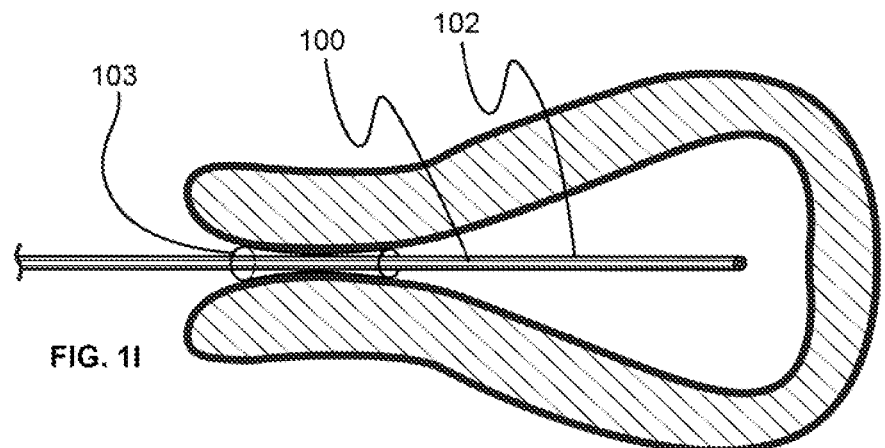
Figure 1J:
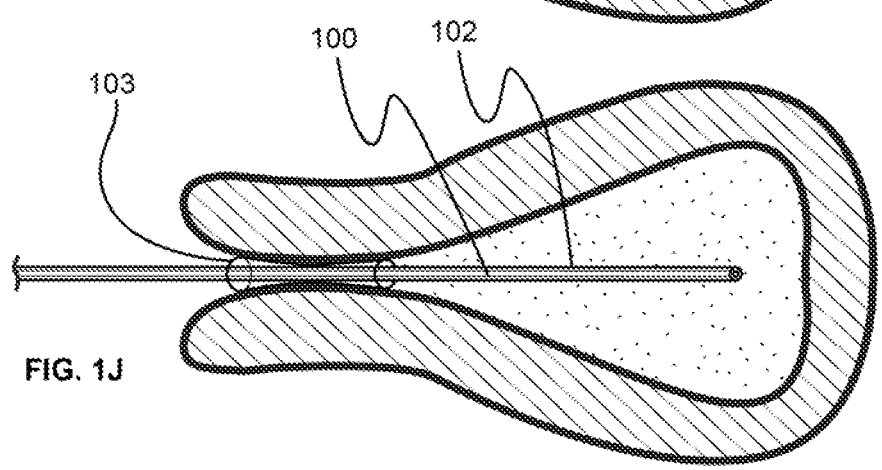
Figure 1K:
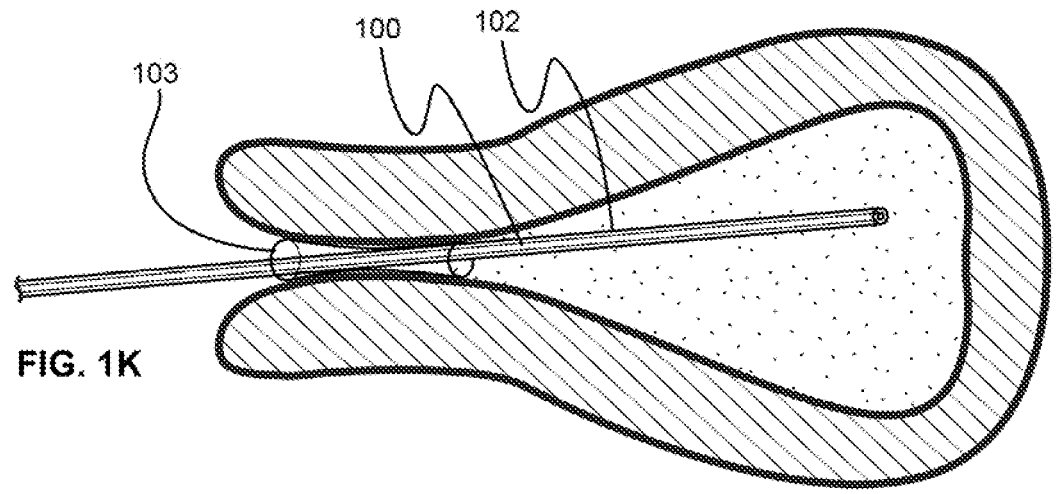
Figure 1L:
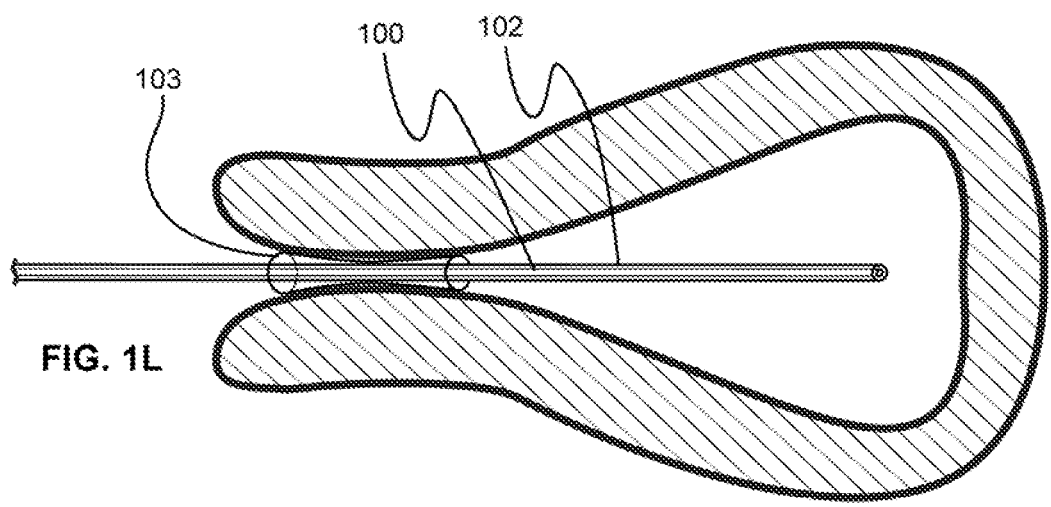
Figure 1M:
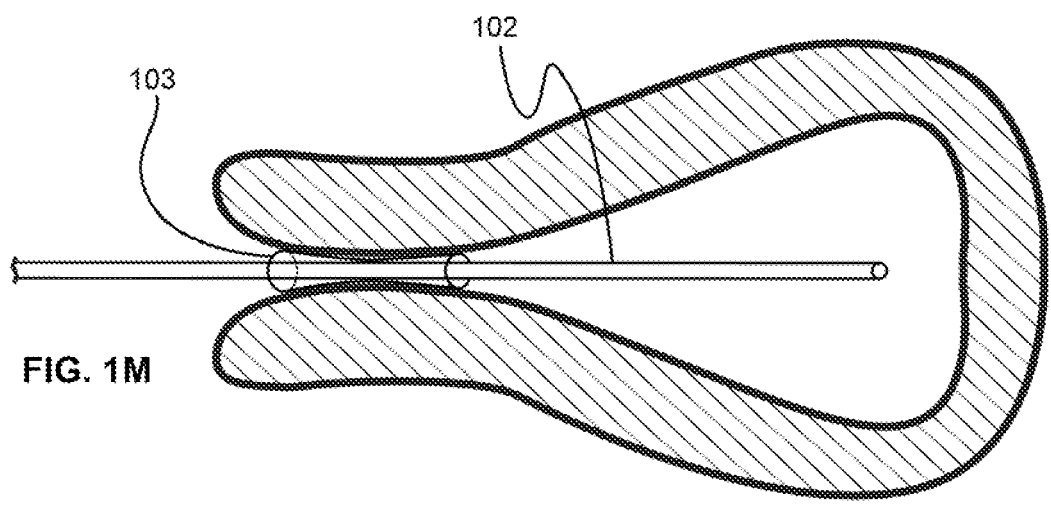

In any of the embodiments disclosed herein, hysteroscope 100 may be inserted using the vaginoscopy or the 'no touch' technique. FIGS. 1H-1P show the steps of a method of treating a uterine cavity using the vaginoscopic technique. In FIG. 1H, the combination of hysteroscope 100, tube 108 and cannula 102 (e.g. such as shown in FIG. 1G) is inserted using the vaginoscopy or the 'no touch' technique. In this technique, the combination is assembled and connected to a source of distension fluid. The flow of distension fluid is started and the combination is inserted into the vagina as shown in FIG. 1B. The vagina gets distended by the distension medium such as flowing saline. The vagina is traversed by gentle movements of the devices to insert them into the cervix through the internal cervical os. This removes the need for using a tenaculum or speculum to assist the introduction of the hysteroscope into the cervix and visualization of the opening of the cervix. This technique has the advantage of being performed without analgesia or anesthesia or using a tenaculum or speculum, thereby saving the time, cost, and effort. It is also easier to perform on obese patients. In FIG. 1I, the hysteroscope combination is inserted further distally into the uterine cavity and a cervical plug 103 is deployed. Examples of plug 103 designs are disclosed elsewhere in this specification. In one embodiment, plug 103 is deployed such that it creates a fluid tight seal in a region of the cervical canal proximal to the internal os. In FIG. 1J, the uterine cavity is then distended by the distension fluid. In this step, one or more diagnostic or therapeutic procedures as disclosed elsewhere in this specification may be performed on the uterine cavity. The hysteroscope combination may be moved to multiple locations within the uterine cavity as shown in FIG. 1K. In FIG. 1L, the distension fluid in the uterine cavity is evacuated. In one embodiment, the distension fluid is evacuated passively by letting the fluid drain out of the cervix. In other embodiments as disclosed elsewhere in this specification, the distension fluid is evacuated actively using one or more user actions. In FIG. 1M, the distal end of cannula 102 is positioned at the desired location within the uterine cavity. Examples of such locations include, but are not limited to: at or near the internal os, at or near a cornu, at or near the fundus, and at or near a mid-cavity region. Thereafter, endoscope 100 and tube 108 are removed from the anatomy leaving behind cannula 102 without dislodging or moving the position of cannula 102. This creates a pathway or access channel into the uterine cavity wherein the proximal end of the channel is present outside the patient's body and the distal end is positioned at the desired location within the uterine cavity as defined by the distal end of cannula 102. The position of plug 103 may be adjusted if needed in any of the steps shown in FIGS. 1I-1P.

Figure 1N:
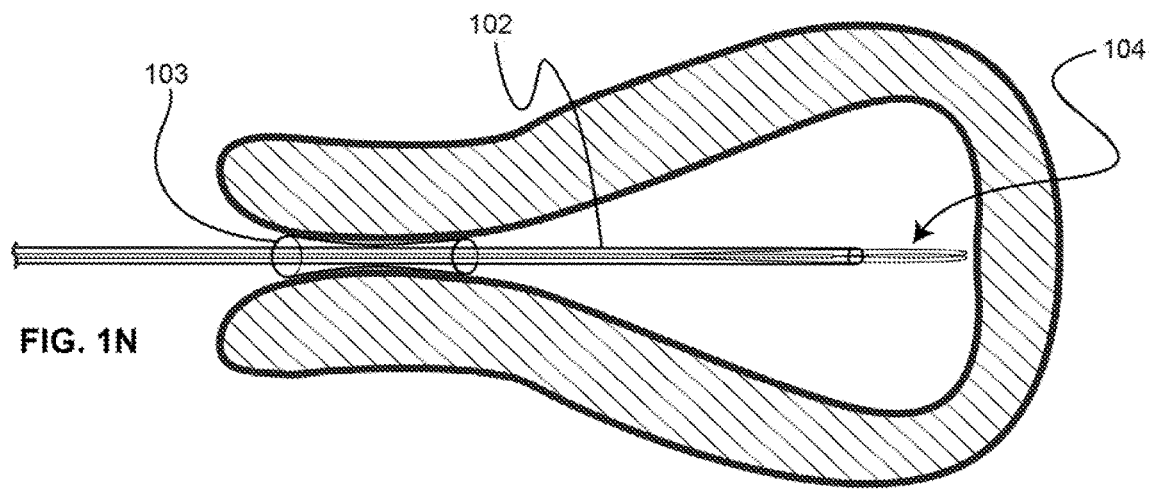

In FIG. 1N, a working device 104 is introduced through cannula 102 into the uterine cavity. Since the distal end of the cannula 102 is positioned at the desired location, the distal end of working device 104 will also emerge at the desired location. Examples of such locations include, but are not limited to: touching the fundus, adjacent to the fundus, adjacent or within a cornu, at the mid corpus region of the cavity, and adjacent or within the internal os.

Figure 1O:
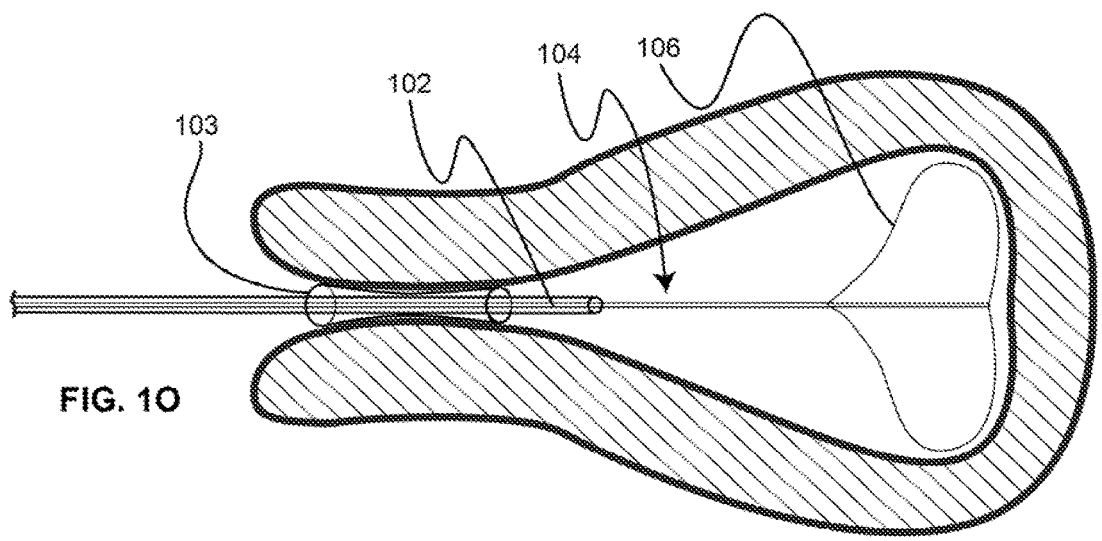

In FIG. 1O, the working device 104 is deployed in the uterine cavity through cannula 102 to perform a medical procedure e.g. a diagnostic, therapeutic, or preventive procedure. A working element on working device 104 may be deployed after working device 104 exits cannula 102 by one or more of: the elastic property of the working element or its components, the super-elastic property of the working element or its components, the shape memory property of the working element or its components, use of a mechanical deployment mechanism for the working element or its components, use of one or more anatomical regions to change the shape of one or more working element portions, etc. Any of the working elements disclosed herein may comprise additional deployment features used to convert a working element from a non-working configuration wherein the working element is incapable of or sub-optimally capable of performing the desired function to a working configuration wherein the working element is capable of performing a desired function. In one embodiment, a pull wire may be used to pull one or more regions of the working element to change the shape of the working element from a non-working configuration to a working configuration. In another embodiment, a sufficiently rigid shaft may be used to push one or more regions of the working element against tissue to change the shape of the working element from a non-working configuration to a working configuration.

In the embodiment shown, working device 104 is an endometrial ablation device and is used to perform an endometrial ablation procedure. In one alternate embodiment, in addition to the introduction of working device 104 through cannula 102, endoscope 100 is re-introduced between the outer surface of cannula 102 and the uterus into the uterine cavity. After performing the diagnostic, therapeutic, or preventive procedure, working device 104 is removed from the anatomy without dislodging or moving the position of cannula 102.

Figure 1P:
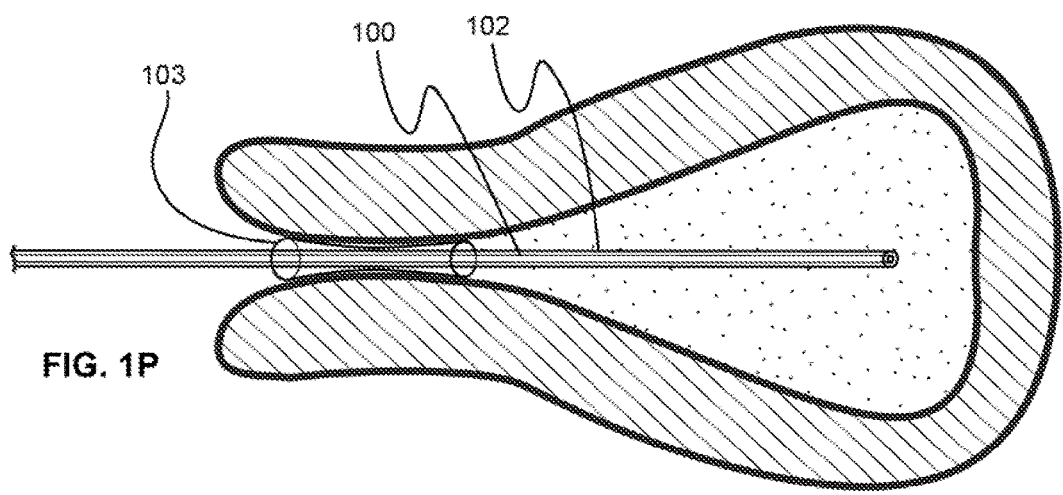

In FIG. 1P, tube 108 and hysteroscope 100 are reintroduced into the anatomy through cannula 102. Thereafter, a check hysteroscopy is performed to see the effect of the procedure performed with working device 104. In one such embodiment, the performance of a therapeutic procedure such as the surface coverage of an endometrial ablation procedure is noted. In other embodiments, parameters such as the location of unablated or untreated regions, location of the lesion relative to a C-section scar, quality of the lesion, etc. are noted. If the performance is found to be inadequate, a repeat procedure may be performed using one or more of the steps disclosed in this specification. Examples of such repeat procedures include, but are not limited to: repeating the endometrial ablation procedure using working device 104 at the same or different locations, using a "spot" ablating device to ablate spots of unablated endometrium, etc. Such repeat procedures may be performed after moving working device 104 to a proximal or distal site in the anatomical region. For example, endometrial ablation procedures may be performed with the first treatment near the fundus and the second treatment at a lower uterine region. In another embodiment, the safety of a procedure is noted using the check hysteroscopy step. For example, the presence of a uterine cavity perforation may be detected using this method. If a perforation is detected, the user may use one or more methods to plug or repair the perforation. This has the advantage that the patient can be treated immediately for any condition that compromises patient safety.

Figure 1Q:
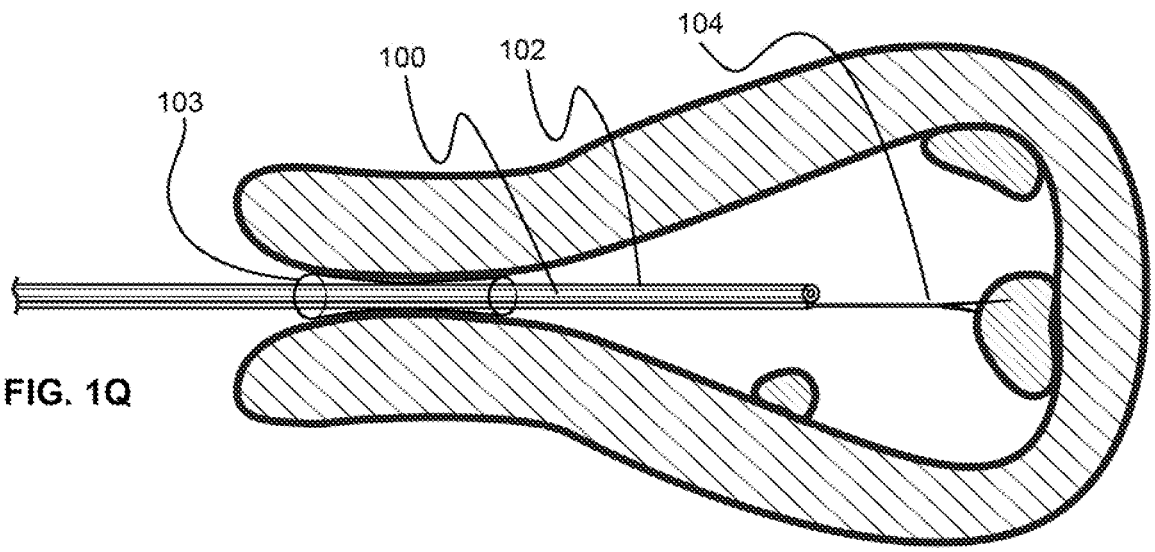
FIG. 1Q shows an embodiment of a hysteroscopic polyp or fibroid removal procedure.

FIG. 1Q shows an embodiment of a hysteroscopic polyp or fibroid removal procedure. In the method shown in FIG. 1Q, any of the method and device embodiments herein may be used to create an access channel to the uterine cavity. Thereafter, a polyp or fibroid removal device 104 (working device 104) is inserted transcervically into the uterine cavity. Working device 104 may be inserted through a channel or lumen of the access channel as disclosed in this specification. Examples of polyp or fibroid removal devices 104 include, but are not limited to: graspers, scissors, scalpel like cutting devices, screws and morcellators. Similar methods may be used to remove blood clots or retained devices from the anatomy such as retained or embedded Intra Uterine Devices.

Figure 1R:
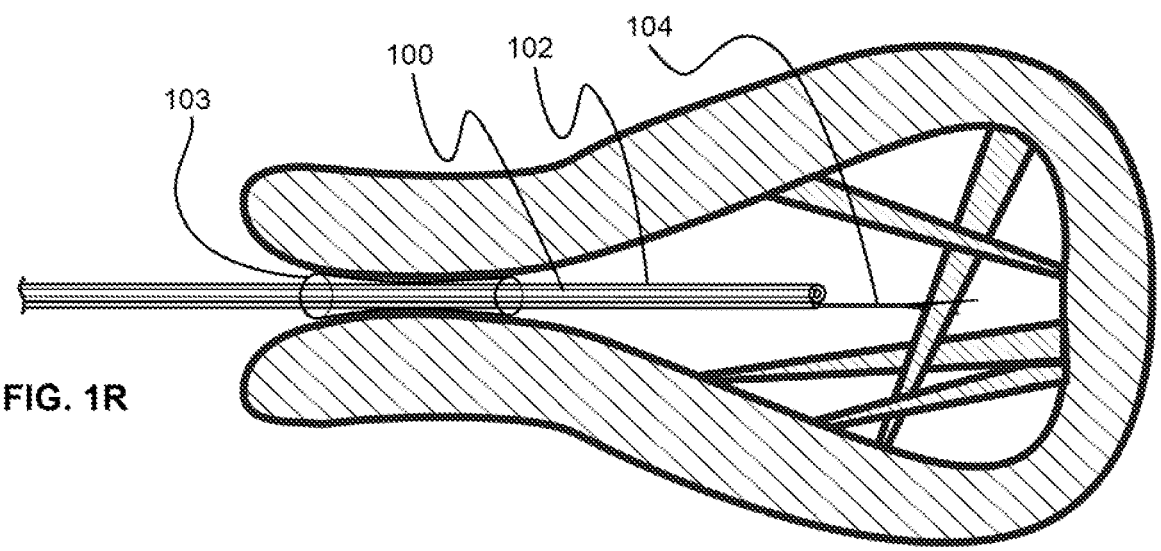
FIG. 1R shows an embodiment of a hysteroscopic adhesion lysis procedure.

FIG. 1R shows an embodiment of a hysteroscopic adhesion lysis procedure. In the method shown in FIG. 1R, any of the method and device embodiments herein may be used to create an access channel to the uterine cavity. Thereafter, an adhesion cutting device 104 (working device 104) is inserted transcervically into the uterine cavity. Working device 104 may be inserted through a channel or lumen of the access channel as disclosed in this specification. Examples of adhesion cutting devices 104 include, but are not limited to: graspers, scissors, hooks, devices with rigid shafts, devices comprising mechanically expandable regions, and electrically powered devices. Similar methods may be used to cut or otherwise remove a septum or sub-septum in the uterine cavity.

Figure 1S:
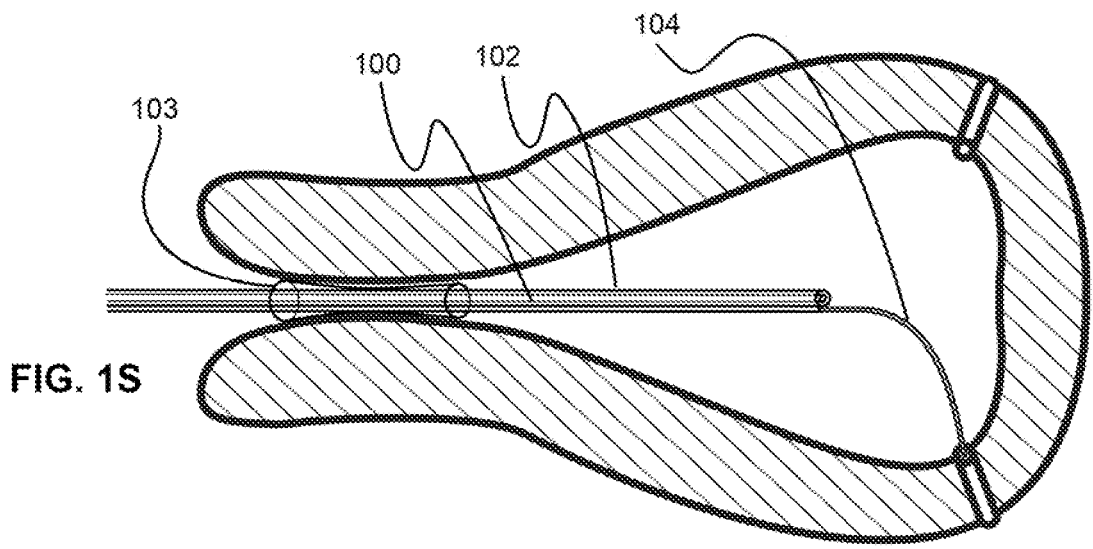
FIG. 1S shows an embodiment of a hysteroscopic tubal occlusion procedure.

FIG. 1S shows an embodiment of a hysteroscopic tubal occlusion procedure. In the method shown in FIG. 1S, any of the method and device embodiments herein may be used to create an access channel to the uterine cavity. Thereafter, a tubal occlusion device 104 (working device 104) is inserted transcervically into the uterine cavity and is navigated through the uterine cavity such that it enters a fallopian tube. Working device 104 may be inserted through a channel or lumen of the access channel as disclosed in this specification. Examples of tubal occlusion devices 104 include, but are not limited to: Essure® device made by Bayer Health-Care Pharmaceuticals, Adiana® device made by Hologic Inc., and other devices that mechanically occlude the fallopian tube lumen.

Figure 1T:
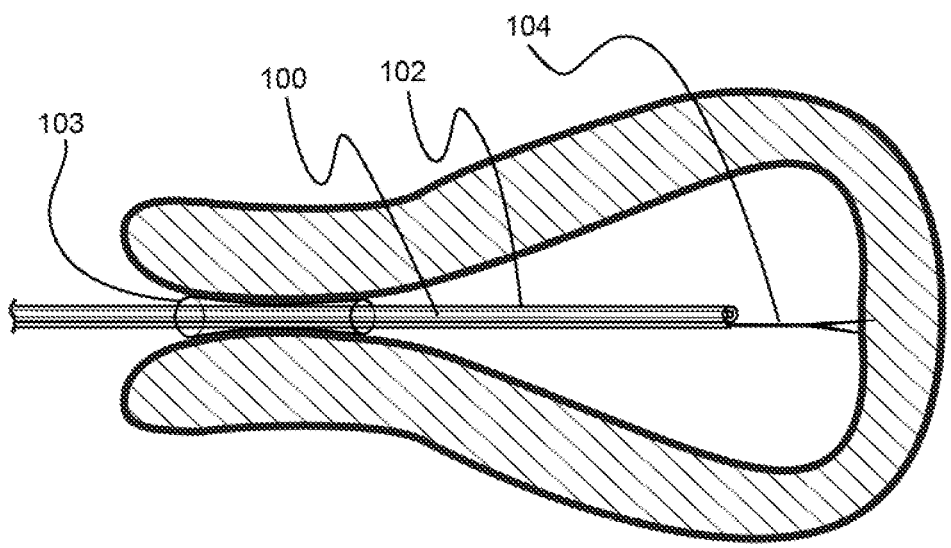
FIG. 1T shows an embodiment of a hysteroscopic targeted biopsy procedure.

FIG. 1T shows an embodiment of a hysteroscopic targeted biopsy procedure. In the method shown in FIG. 1T, any of the method and device embodiments herein may be used to create an access channel to the uterine cavity. Thereafter, a biopsy device 104 (working device 104) is inserted transcervically into the uterine cavity. Working device 104 may be inserted through a channel or lumen of the access channel as disclosed in this specification. The distal end of the biopsy device 104 is navigated to a target region of interest. Thereafter, biopsy device 104 is used to take a biopsy of the target region. Examples of biopsy devices 104 include, but are not limited to: cutting devices, and suction based biopsy devices.

Figure 1U:
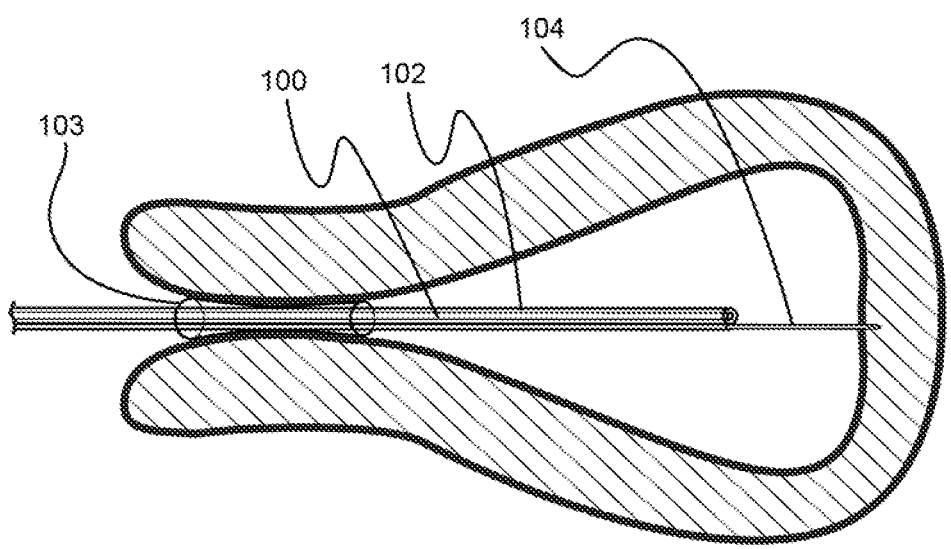
FIG. 1U shows an embodiment of a hysteroscopic injection procedure.

FIG. 1U shows an embodiment of a hysteroscopic injection procedure. In the method shown in FIG. 1U, any of the method and device embodiments herein may be used to create an access channel to the uterine cavity. Thereafter, an injecting device 104 (working device 104) is inserted transcervically into the uterine cavity. Working device 104 may be inserted through a channel or lumen of the access channel as disclosed in this specification. The distal end of the injecting device 104 is navigated to and used to penetrate one or more target regions of interest such as a region near the mid-fundus, a region near the cornua, a region near the center of the uterine cavity, etc. In one embodiment, injecting device 104 is used to inject a local anesthetic into one or more regions of the uterus. Examples of injecting devices 104 include, but are not limited to: needles, powered injection devices, scissors, scrapers and syringe based injection devices.

Any of the method embodiments shown in FIGS. 1Q-1U may be used before or after an endometrial ablation procedure. Any of the device manipulations shown herein may be used to perform the method embodiments in FIGS. 1Q-1U.

Although the specification discloses methods for accurate placement of devices in the anatomy, in some situations, it is useful to have an independent method of confirming the position of device 104 and/or the proper deployment of antenna 106 and other working elements located on device 104. In one embodiment, a measured insertion depth of device 104 is compared with an expected insertion depth to check for correct placement of device 104. In one embodiment, resistance to further insertion of device 104 is used to check for correct placement of device 104. This may happen for example, if device 104 is against the uterine fundus or against the distal end of an anatomical region. In another embodiment, a returned power level of a microwave energy delivered to device 104 is used to check for the correct position of device 104 and/or the proper deployment of antenna 106. Examples of such methods are disclosed in US Patent Application Publications 2014/0190960, 2010/0121319, 2010/0137857, 2013/0256302, 2010/0125269 and related patent documents, the entire disclosures of which are incorporated herein by reference. In one such embodiment, a returned power level is used to check for placement of a working element 106 in one or more of: the distal-most region, the proximal-most region, the widest region, the narrowest region, and a region having a distorting lesion of an anatomical region. In another such embodiment, one or more returned power measurements are used to check for the full deployment of a working element 106. In one embodiment, full deployment of working element 106 is defined as working element 106 deployed to the greatest transverse or longitudinal (at right angles to the long axis of the body) dimension that is mechanically possible in the anatomical region. In another embodiment, full deployment of working element 106 is defined as working element 106 deployed to the greatest volume that is mechanically possible in the anatomical region. A medical procedure using working device 104 may be terminated or prevented from starting if the position and/or deployment of working device 104 and/or antenna 106 are improper.

Various other methods and devices may be used to check for the position and/or deployment of working device 104 and/or working element 106. In one such embodiment, the position and/or deployment of a balloon is checked by measuring one of: a pressure inside the balloon, an inflation volume of the balloon, temperature of a region inside or outside the balloon, and a dimension of the balloon. Examples of such methods and devices are disclosed in United States Patent Applications 2015/0045780, 2014/0012156, and 2014/0005650. In another embodiment, the position and/or deployment of a working element 106 is checked by measuring one of: measuring the width of working element 106 (e.g. by imaging, by a mechanical indicator of the width, etc.), comparing the width of deployed working element 106 with the width of an anatomical region measured before inserting the working element 106 (e.g. checking the deployed width of working element 106 with endoscopically or radiologically measured pre-procedure width of an anatomical region), checking the perforation of an insertion tract or an anatomical region (e.g. by delivering a fluid and measuring the pressure or the volume of the fluid introduced in the anatomy), etc. Examples of such methods and devices are also disclosed in United States Patent Applications 2011/0112432, 2011/0112523, 2012/0116378, and 2014/0214020, and in U.S. Pat. Nos. 6,743,184 and 6,872,183. In another embodiment, the position and/or deployment of working device 104 and/or working element 106 is checked by one of: comparing a measured insertion depth of working device 104 with an expected insertion depth, measuring the level of pain or discomfort felt by a patient using an imaging modality, and feeling a resistance to insertion of working device 104.

Figure 2A:
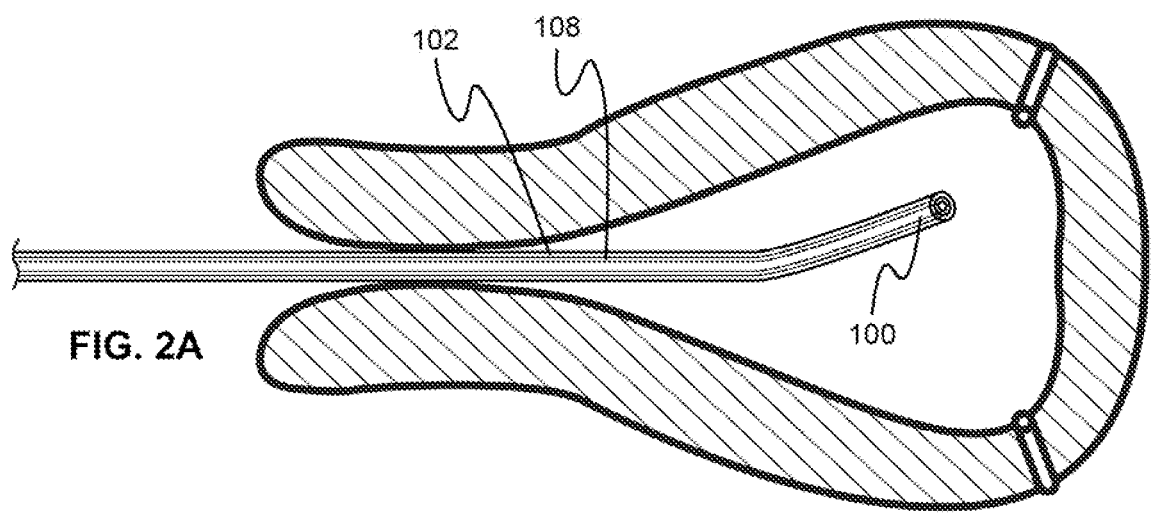
FIG. 2A shows one embodiment of a cannula comprising a steering mechanism.

FIG. 2A shows one embodiment of cannula 102 comprising a steering mechanism. Steering mechanism shown is a stiff, pre-shaped, hollow tube 108 that slides within a lumen of cannula 102. In the embodiment shown in FIG. 2A, tube 108 is located in the same lumen as endoscope 100. In alternate embodiments, tube 108 is located in a separate lumen as endoscope 100. The distal region of tube 108 is pre-shaped and has a non-linear shape that is sufficiently stiff to retain its shape when endoscope 100 is advanced through cannula 102. In the embodiment shown, cannula 102 has a lumen through which tube 108 is slidably positioned. Tube 108 in turn has a lumen through which endoscope 100 is slidably positioned. In one method embodiment, the combination of cannula 102, tube 108 and endoscope 100 is introduced in the anatomy e.g. the uterine cavity through a natural path e.g. the cervix under endoscopic guidance. Thereafter, the distal end of cannula 102 is positioned at the desired location e.g. the mid fundus location or near a cornu by manipulating the stiff combination of cannula 102, tube 108 and endoscope 100 under endoscopic guidance. Examples of such manipulations include, but are not limited to: rotating the combination, pulling or pushing the combination, twisting the combination using the cervix as a lever, and engaging a shape changing modality of a device of the combination. The added stiffness and/or the non-linear distal region of tube 108 are advantageous over the mere combination of cannula 102 and endoscope 100 since they enhance the pushability and steerability of the distal region of cannula 102. Thereafter, endoscope 100 with or without tube 108 is removed leaving behind an access channel defined by cannula 102. The access channel can then be used to introduce devices or fluids as disclosed elsewhere in this specification. Another advantage of having a system comprising tube 108 is that the added stiffness of tube 108 limits bending of endoscope 100 thereby preventing damage to endoscope 100 by the mechanical forces exerted on it when it is bent more than a safe threshold. In an alternate embodiment, the distal region of cannula 102 itself is pre-shaped and has a non-linear shape that is sufficiently stiff to retain its shape when endoscope 100 is advanced through cannula 102.

Figure 2B:
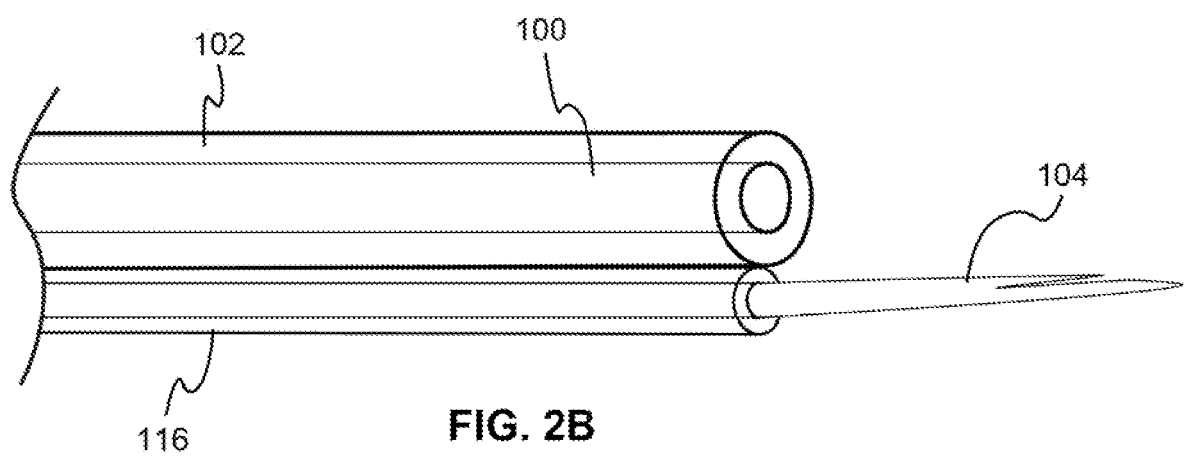
FIG. 2B shows a first embodiment of a cannula comprising an additional lumen for the transport of devices or fluids.

FIG. 2B shows a first embodiment of cannula 102 comprising an additional lumen 116 for the transport of devices or fluids. Lumen 116 may be collapsible or rigid. Lumen 116 is in addition to a lumen of cannula 102 through which endoscope 100 is inserted. In the embodiment shown, device 104 is an elongate needle with an injection lumen for injecting fluids into or adjacent to tissue. In one method embodiment, needle 104 is used to inject local anesthetics into uterine or cervical tissue during a trans-cervical procedure. In one such embodiment, local anesthetics are injected into uterine tissue (e.g. in the fundal region, in the cornual regions, etc.) before an endometrial ablation procedure. This can be performed under endoscopic guidance. Thereafter, needle 104 is removed along with endoscope 100. An endometrial ablation device is then introduced through a lumen of cannula 102 to perform an endometrial ablation procedure. In another embodiment, needle 104 is inserted through the same lumen as the lumen through which endoscope 100 is introduced. Lumen 116 may also be used for transport of fluids as disclosed elsewhere in this specification.

Figure 2C:
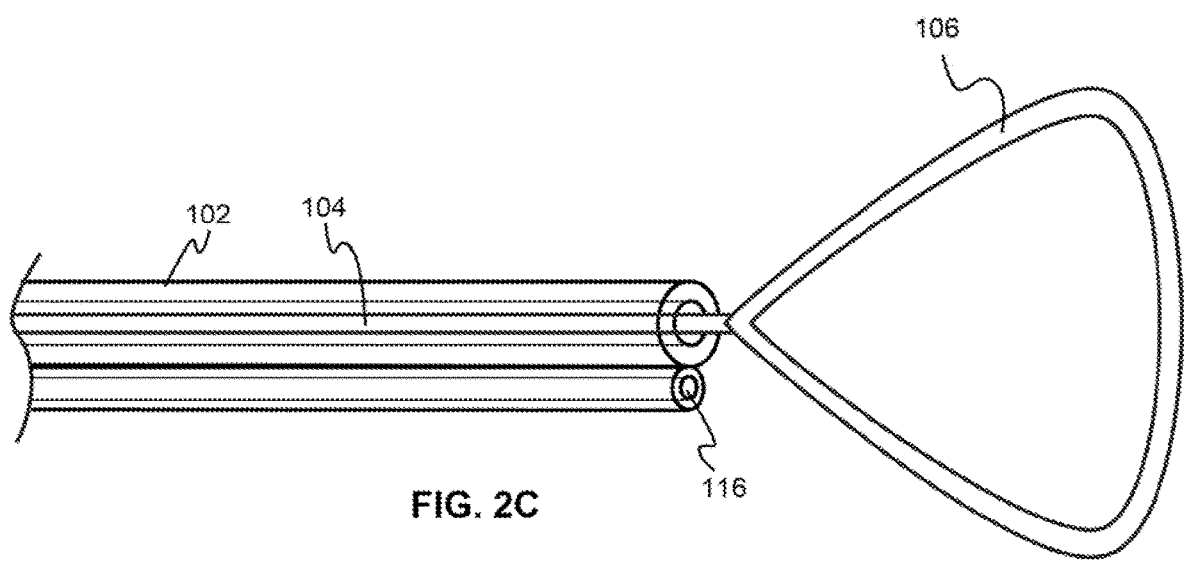
FIG. 2C shows a second embodiment of a cannula comprising an additional lumen for the transport of devices or fluids.

FIG. 2C shows a second embodiment of cannula 102 comprising an additional lumen 116 for the transport of devices or fluids. In this embodiment, Lumen 116 is sufficiently rigid such that it does not significantly collapse during a procedure. Lumen 116 is in addition to a lumen of cannula 102 through which endoscope 100 is inserted. Lumen 116 may be used for transport of fluids as disclosed elsewhere in this specification. In one embodiment, lumen 116 is used for the transport of a distension medium as disclosed elsewhere in this specification. Lumen 116 may be rigid or collapsible. Lumen 116 may be adjustable along the length of cannula 102. Device 104 may be any of the elongate devices mentioned in this specification, including, but not limited to the endometrial ablation devices disclosed in US 2010/0121319, US 2010/0137857, US 2013/0256302 and related applications.

Any of the embodiments of cannula 102 disclosed herein may be used to insert an adjunct device into the anatomy. The adjunct device may be inserted before, after, or simultaneously along with the primary working device. In one embodiment, the adjunct device is a needle that is used for performing any of the methods disclosed herein. In one embodiment, the adjunct device is a sensor used for sensing a condition of the tissue or a device. Examples of sensors include, but are not limited to: temperature sensors, temperature sensors, impedance sensors, electrophysiological signal sensors, visualization elements, flow sensors, Doppler effect sensors, and pressure sensors. In one example, the pressure sensor is a sensor for measuring the pressure in a cavity or lumen (e.g. the uterine cavity). In another example, the pressure sensor is a sensor for measuring the pressure and/or contact of a device against a bodily surface (e.g. the uterine fundus). In one example, the adjunct device is a temperature sensor used to determine the boundary of an ablation. This information may be used to stop the energy delivery during an ablation procedure. In one example, the adjunct device is a temperature sensor inserted into and used to determine the temperature of and organ or tissue (e.g. uterine serosa, bladder, bowel) surrounding a target organ (e.g. the uterus). Such sensors may be present on any of the devices disclosed herein.

The adjunct device may penetrate into a tissue. Examples of such tissue regions include, but are not limited to: walls of a lumen, walls of an anatomical cavity, solid mass of a tissue, natural anatomical passages, and surgically created anatomical passages. In one such example, the adjunct device is penetrated into the uterine wall. In another such example, the adjunct device is penetrated beyond the uterine myometrium into the uterine serosal or adjacent to the bowel or bladder.

Further examples of adjunct procedures that may be performed along with any of the embodiments disclosed herein include, but are not limited to:

1. Removal of lesions or other material from a bodily region. Examples of such lesions or other material include, but are not limited to: fibroids, polyps, adhesions or scarring, septum or sub-septum, and blood clots,
2. Biopsy procedures (e.g. endoscope guided biopsy),
3. Plugging or blocking a lumen such as a blood vessel, fallopian tubes (e.g. using an implant, fusing the cornus using tissue sealing methods) for contraception), ducts, glands, etc.,
4. Removal of devices such as contraceptive implants, embedded devices, and mis-positioned or migrated devices,
5. Removal of fluids such as liquids from a target anatomy,
6. Injecting or infusing anesthetic (e.g. an anesthetic liquid or gel) into an anatomical region. In one such embodiment, a local anesthetic is injected at one or more regions (e.g. fundal region, cornua, mid uterine region, cervix, lower uterine region) in the uterine wall or around the uterus. The anesthetic may be introduced before, during, or after a treatment,
7. Injecting or infusing hot fluids into the anatomy,
8. Injecting or infusing drugs or other chemicals into the anatomy,
9. Scraping an anatomical region (e.g. a dilation & curettage like procedure),
10. Delivering photodynamic therapy
11. Morcellating tissue
12. Delivering UV light to cause a change in tissue material or a chemical material. Such procedures may be used for example to plug anatomical passages and lumens such as the fallopian tubes,
13. Sterilizing or disinfecting a region of the body. Examples of such methods include methods for inserting sterilizing chemicals such as antibiotics or disinfectants or UV light.
14. Injecting or infusing chemicals or inserting devices for preventing scarring or adhesions after a procedure. Examples of such chemicals include, but are not limited to: gels, mechanical barriers such as coils or sheets, intrauterine devices such as Mirena®, drug infusions, removable balloons, sprays of barrier agents, oils and other hydrophobic substances, proprietary barriers (e.g. Interceed, Seprafilm, Adept, Hyalobarrier, SprayShield, PrevAdh, and Intercoat), and infusing a cryogenic or low temperature material,
15. Removing ablated tissue,
16. Placing an implant post-procedure. Examples of such procedures are placing a levonorgestrel eluting implant post an endometrial ablation procedure, and
17. Dilating a canal or tract of the body or an artificially created opening in the body under endoscopic guidance. Examples of such procedures include dilating the cervical canal under visual guidance.

Figure 2D:
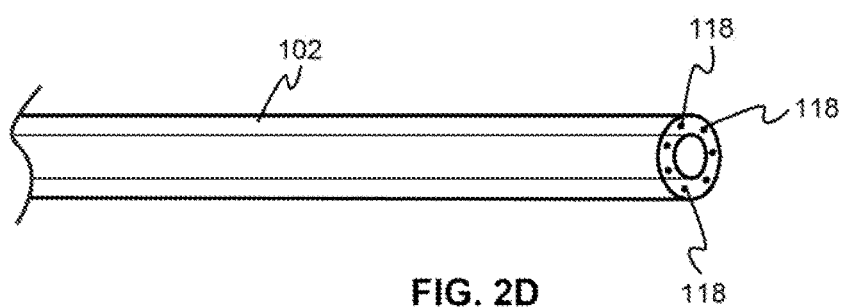
FIG. 2D shows an embodiment of a cannula comprising integrated visualization or illumination elements.

Any of the adjunct procedures disclosed herein may be performed before, after, or during a primary procedure. Examples of adjunct procedures or adjunct device disclosed herein may also be used as primary procedures or working devices 104 respectively FIG. 2D shows an embodiment of a cannula 102 comprising integrated visualization or illumination elements 118. Visualization or illumination elements 18 may be one or more of: Fiberoptic illumination elements, Fiberoptic imaging elements, and endoscopic imaging elements. In one embodiment, integrated visualization or illumination elements 118 are used instead of or in conjunction with endoscope 100 inserted through a lumen of cannula 102. The proximal region of illumination elements is connected to a source of light. The proximal region of visualization elements is connected to an optical or electronic means to enable a user to view the endoscopic images.

Figure 2E:
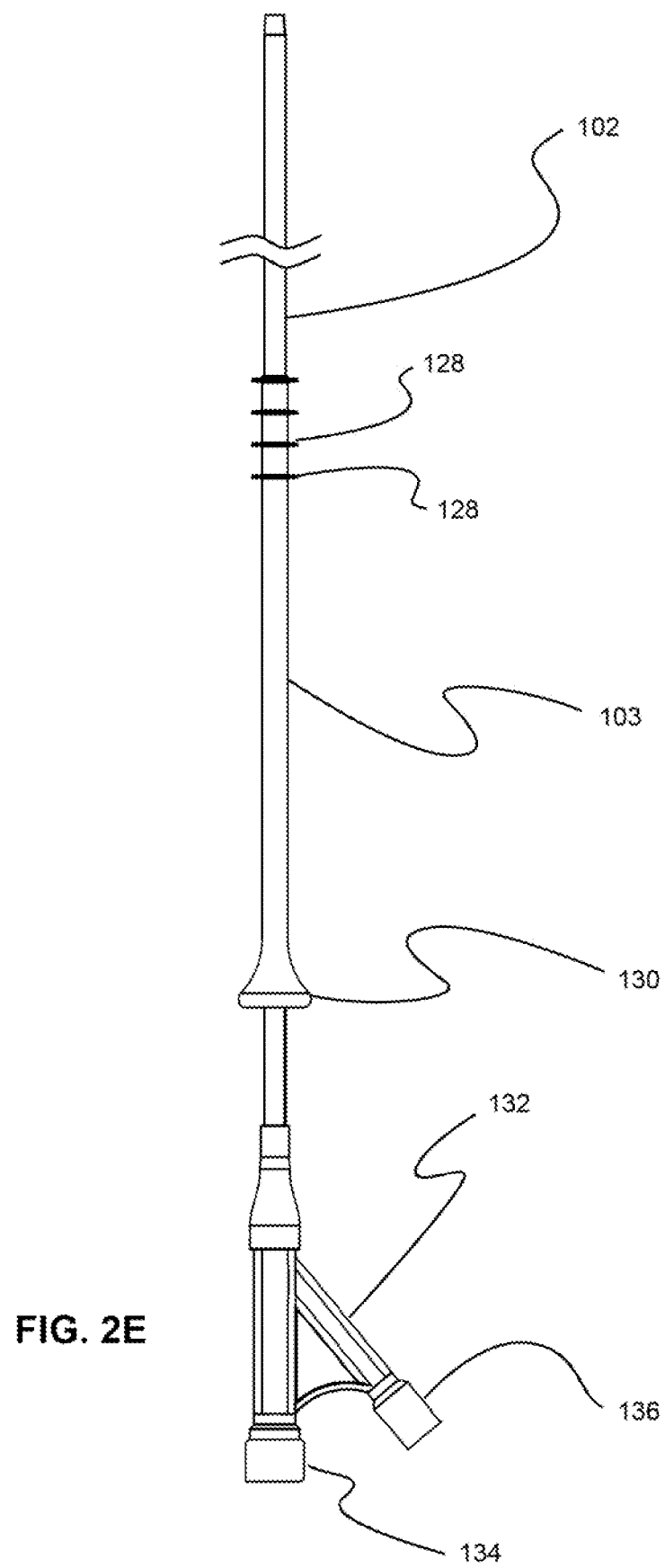
FIG. 2E is a side view of an embodiment of a cannula comprising a plug.

FIG. 2E is a side view of an embodiment of cannula 102 comprising a plug 103. Plug 103 is elongate in shape and comprises multiple fins 128 on its outer surface. Plug 103 comprises between one to 20 fins 128. The size of fins 128 may vary along the length of plug 103. The proximal end of plug 103 comprises an enlarged grip 130 that allows a user to grip plug 103 to adjust its position along cannula 102. Plug 103 may be made of rigid, flexible or semi-rigid biocompatible materials such as: polymers, silicones, ceramics, and rubbers. The length of plug 103 may range from 0.5 to 20 centimeters. Fins 128 are designed to seal the area between the outer surface of cannula 102 and the surrounding anatomy. Fins 128 may be flexible or substantially rigid. The outer diameter of fins 128 may range from two mm to 15 mm. In one embodiment, the length of plug 103 is fixed and the location of the distal end of plug 103 is determined from the location of the proximal end of plug 103 on the outer surface of cannula 102. Any cannula 102 or any other device disclosed herein may comprise one or more visual markings on their outer surface. Such markings may be used to determine the location of the distal end of plug 103 as described above. This method is especially useful if the distal end of plug 103 is within the anatomy and is not visible to the user. The location of plug 103 on the cannula 102 may be adjusted as needed. In one embodiment, the adjustment is done based on measurements of one or more anatomical dimensions obtained during or before a procedure. Plug 103 may be transparent or opaque. In the embodiments containing a transparent plug 103, the user may determine the position of plug 103 by reading one or more visual markings on their outer surface of cannula 102 through plug 103. The distal tip of plug 103 may be tapered. Any of plugs 103 disclosed herein may be a separate device that is slidable or otherwise repositionable over cannula 102. Alternately, any of plugs 103 disclosed herein may be integrated or fixed to cannula 102. Any of the plugs 103 disclosed herein may comprise a lubricious liner made of a lubricious material include, but not limited to: Teflon and FEP to reduce the friction between plug 103 and cannula 102.

Plug 103 is designed to provide a complete or partial fluid tight seal against the cervix such that fluids introduced or present in the uterine cavity do not leak out through the cervix. In one embodiment, plug 103 is also designed to abut against the external portion of the cervix and thereby limit the insertion depth of cannula 102. The position of plug 103 relative to the shaft of cannula 102 may be adjustable. The length of plug 103 is fixed and may be provided to the user. Further, the cannula 102 has visual markings on its surface as shown to know the depth of insertion of cannula 102 in the anatomy. Using the visual markings on the cannula 102 surface, the location of distal end of plug 103 may be calculated from the location of the proximal end of plug 103. The position of plug 103 relative to the position of the shaft of cannula 102 may be reversibly lockable. In one method embodiment, the desired depth of insertion of cannula 102 is determined by one or more of uterine sounding, hysteroscopy and ultrasonography. The desired depth may be calculated by measuring uterine parameters including, but not limited to: uterine sounding length, uterine cavity length, and cervical canal length. Thereafter, cannula 102 is inserted into the uterine cavity. Thereafter, the position of plug 103 relative to the distal end of cannula 102 is adjusted. In one embodiment, the position of plug 103 is adjusted such that the distal end of plug 103 is located inside the cervical canal, but proximal to the internal os. Plug 103 acts as an external seal to create a fluid tight seal of the cervical canal. In one embodiment, plug 103 limits the depth of insertion of the distal end of cannula 102 thereby reducing the risk of uterine perforation while also ensuring optimal placement of a working device 104 relative to the target tissue. The device and method embodiment of FIG. 2E may be used in any of the device and method embodiments disclosed herein.

In an alternate embodiment, plug 103 is made of compressible foam and has a tapered distal end. The foam material may be a biocompatible material including, but not limited to: polymers (e.g. Teflon, E-PTFE, polyethylene, etc.), metals, silicones, and rubbers.

Visual markings may also be present on one or more regions of devices disclosed herein including, but not limited to: endoscope 100, device 104, and antenna 106. Such markings may be visualized by one or more of: direct visual observation by a user and endoscopic visualization. In one embodiment, one or more visual markings on the surface of a devices disclosed herein (e.g. device 104) are used to check the depth of insertion of the device into the anatomy. For example, a pre-procedure measured uterine sounding length measured by uterine sounding, imaging, etc. is used to arrive at an estimated insertion depth of the device. If the measured uterine insertion depth of the device is similar to the estimated insertion depth, then it can be concluded that the device is inserted in the correct position. Similar methods can be used for confirming the position of device 104 and other devices disclosed herein after they are inserted in the anatomy using any of the methods disclosed herein. Visual markings may also be used to reposition cannula 104 and other access channels disclosed herein if they have inadvertently moved during a procedure.

Cannula 102 in FIG. 2E comprises a proximal hub 132 that is used for introducing devices and/or fluids into the anatomy. In the embodiment shown, a proximal seal 134 provides a fluid tight seal around a lumen through which a device such as working device 104 or a hysteroscope 100 is introduced. Examples of elements that can provide a fluid tight seal include, but are not limited to: valves, check valves, dual check valves, rotating hemostasis valves, Tuohy Borst valves, manually opening valves, and caps. In one embodiment, a working device 104 is introduced through proximal seal 134. Thereafter proximal seal 134 is sealed either manually or automatically and a fluid is introduced through cannula 102. Proximal seal 134 prevents the leakage of fluid between working device 104 and cannula 102. Cannula 102 in FIG. 2E further comprises a side port 136 that is in fluid communication with the distal region or tip of cannula 102. Side port 136 may be used for one or more of: draining or venting the fluids present in the anatomy surrounding the distal region of cannula 102 to the patient's exterior, inserting or withdrawing fluids, applying a vacuum, and inserting or withdrawing adjunct devices.

Figure 2F:
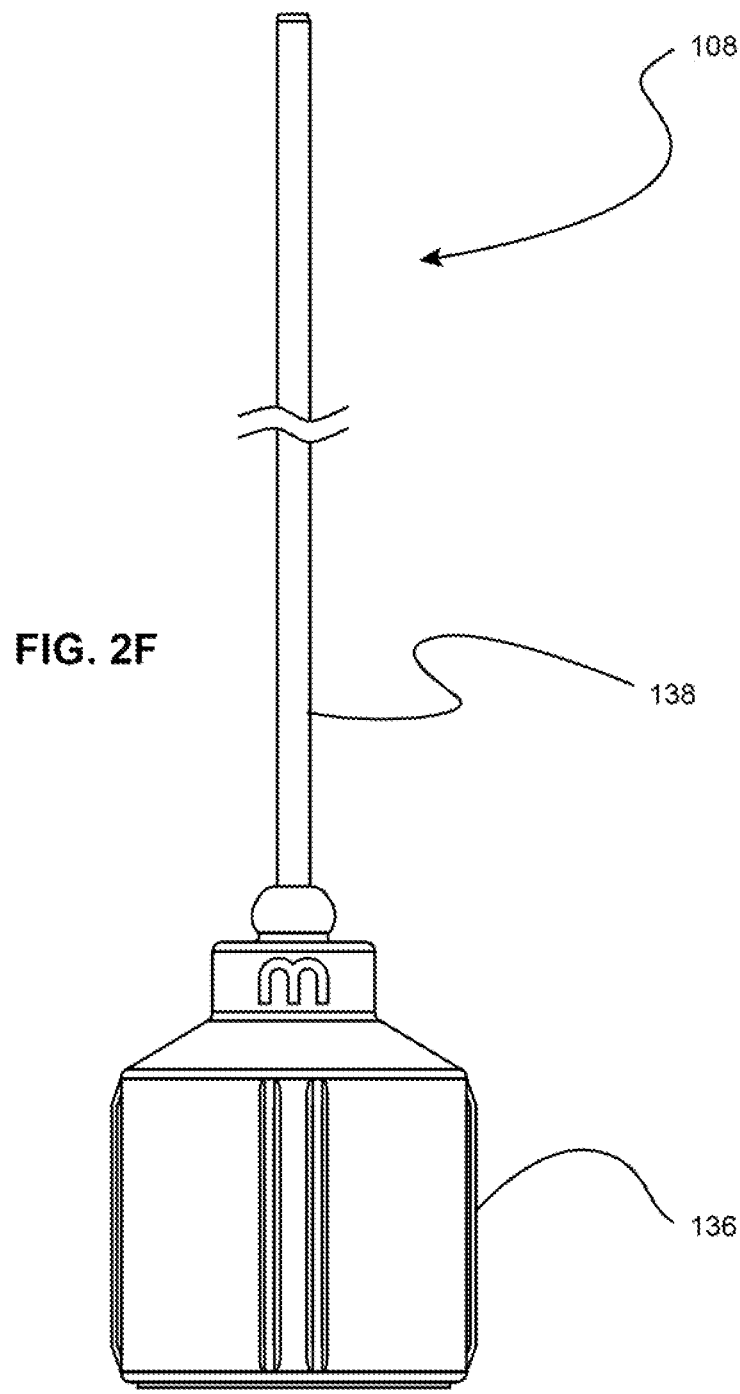
FIG. 2F shows a side view of an embodiment of a tube that can be used with a cannula disclosed herein.

FIG. 2F shows a side view of an embodiment of a tube 108 that can be used with a cannula 102 disclosed herein. Tube 108 comprises a proximal cap 137 and a distal hollow shaft 139. The length of tube 108 is such that when tube 108 is inserted into cannula 102, the distal end of tube 108 is located close to the distal end of cannula 102. During use, tube 108 is inserted into cannula 102 until the distal region of proximal cap 137 touches the proximal end of cannula 102. Tube 108 and cannula 102 may be designed such that they temporarily lock into each other. In one such embodiment, a region of tube 108 locks into a region of cannula 102 by a frictional fit. During use (e.g. as shown in FIG. 1G), when a user introduced hysteroscope 100 through tube 108, stiff, hollow proximal cap 137 covers the transition region of hysteroscope 100 between a proximal hub and the shaft containing the optics. Since the transition region of hysteroscope 100 is often the mechanically weakest region during use, proximal cap 137 helps in preventing breakage of hysteroscope 100 by providing additional mechanical strength. Further, distal hollow shaft 139 is sufficiently stiff to give an additional mechanical protection of the hysteroscope shaft 100 containing the optics. In this way, tube 108 mechanically protects hysteroscope 100 during use from the forces and torques experienced by hysteroscope 100 during use. In one embodiment, tube 108 has a total length of about 2-50 cm wherein the proximal cap 137 has a length of about 0.5-5 cm and the distal hollow shaft 139 has a length of about 1.5-50 cm. Tube 108 may be made of a variety of biocompatible metals, plastics, etc. In one embodiment, proximal cap 137 is made of a silicon over-mold over a plastic base and shaft 139 is made of a biocompatible metal. The distal end of proximal cap 137 may comprise a locking mechanism to reversible lock with a proximal region of cannula 102.

Figure 2G:
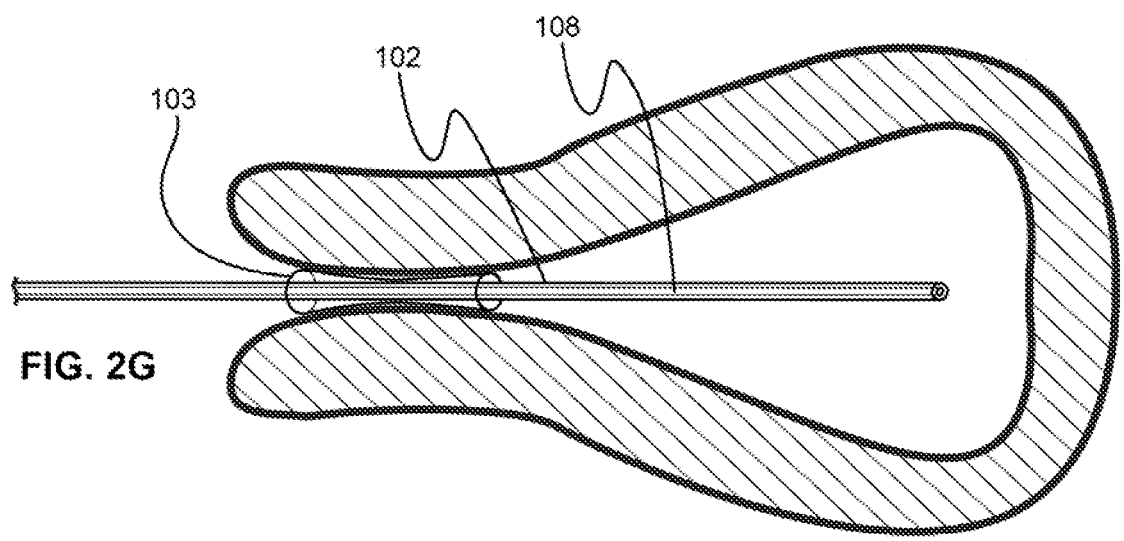
FIG. 2G shows an embodiment of a method of creating an access channel into an anatomical region without using an endoscope.
Figure 3A:
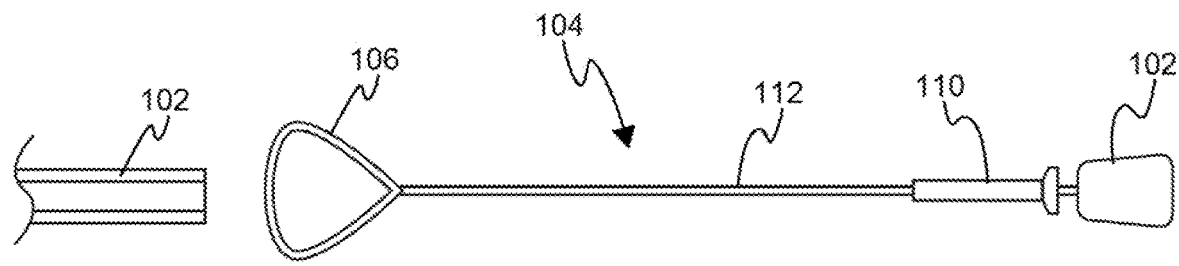
FIGS. 3A-3D show one embodiment of introducing a medical device through a low profile access path created by a cannula.
Figure 3B:
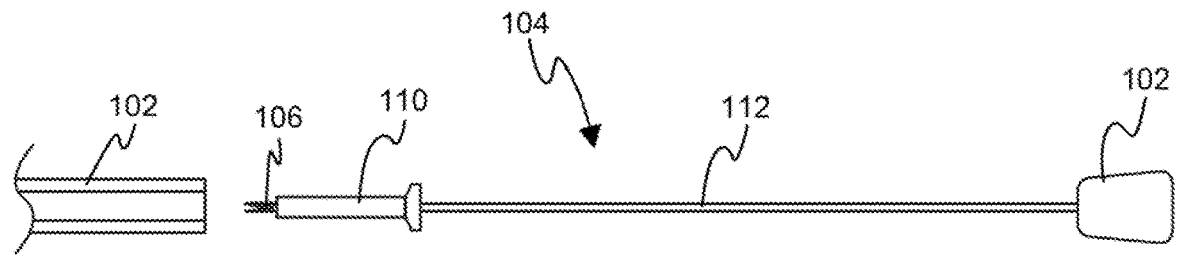
Figure 3C:
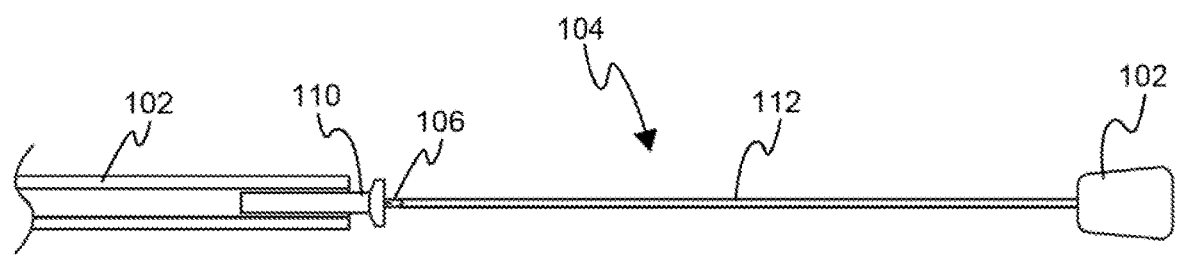
Figure 3D:
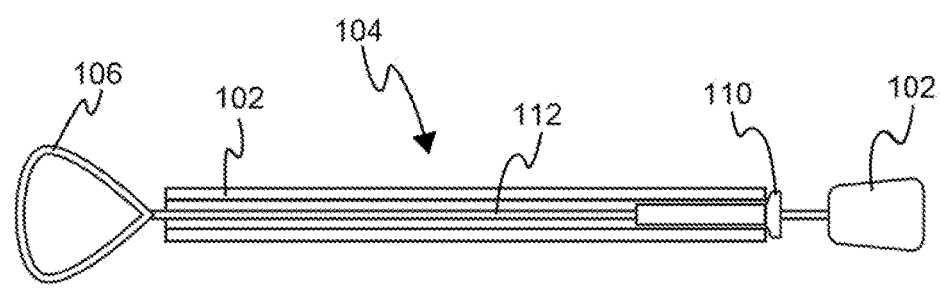

FIG. 2G shows an embodiment of a method of creating an access channel into an anatomical region without using an endoscope. In this method, a stiff tube 108 is inserted into a relatively flexible cannula 102. The combination is then inserted into the uterine cavity without using a endoscope.

Any of the lumens of any cannula 102 disclosed herein may be coated or lined with a lubricious material to enable easy introduction of one or more devices through the lumen. Examples of such lubricious materials include, but are not limited to: Teflon and FEP. The stiffness of cannula 102 may vary along its length. In one such embodiment, the distal region of cannula 102 is more flexible than the proximal region of cannula 102. Any of the devices and/or lumens disclosed herein may have a circular or non-circular cross-section. Examples of non-circular cross section shapes include, but are not limited to round, oval, rectangular, triangular, elliptical, square, etc. Any of the devices disclosed herein may comprise one or more pre-shaped regions.

Any cannula 102 disclosed herein may comprise one or more channels or access paths to introduce one or more devices or fluids into the anatomy. The one or more channels may be fixed (the dimensions of the channel stay constant through a procedure) or may be expandable and collapsible (the dimensions of the channel vary through a procedure depending on the presence of fluids or devices). A fluid channel may be used for introducing or draining fluids from the anatomy. The fluid may be continuously introduced in the anatomy for flushing or distending a cavity. Cannula 102 may comprise one or more sealing mechanisms to seal one or more regions of the cannula 102 or a region between cannula 102 and the tissue. The sealing mechanism may be used to create a fluid tight seal such that bodily fluids or fluids introduced during a procedure don't leak or minimally leak around the sealing mechanism. The sealing mechanism may be integrally attached to cannula 102 or may be slidably attached or detachably attached to cannula 102. Examples of sealing mechanisms include, but are not limited to: plugs, expandable compliant or non-compliant or semi-compliant balloons, tapered solid surfaces, foam or other soft and compliant materials, and stoppers. In one embodiment, a slidable cervical sealing mechanism made of silicone is slidably positioned over cannula 102 to plug or seal the cervical canal. The cervical sealing plug or seal may comprise one ore more of: tapered regions, soft multiple fins, and expandable structures.

Any cannula 102 disclosed herein may be used to introduce and/or remove one or more fluids into the anatomy. In one embodiment, cannula 102 comprises a fluid transport lumen. The fluid transport lumen extends from a proximal region of cannula 102 till a distal region of cannula 102 that is placed inside the anatomical cavity. In one embodiment, the fluid transport lumen is an additional lumen separate from the lumen used for inserting endoscope 100 or device 104. In another embodiment, the fluid transport lumen is defined by the gap between the lumen used for inserting endoscope 100 or device 104 and the outer surface of endoscope 100 or device 104. The fluid transport lumen may be used for one or more of: evacuating liquids or gases from an anatomical region; introducing liquids inside an anatomical region such as anesthetics, contrast agents, cauterizing agents, alcohols, thermal cooling agents, thermal heating agents, a fluid dielectric medium that surrounds antenna 104, antibiotics and other drugs, saline and flushing solutions, distension media; introducing gases for detecting perforation of organs such as the uterus; evacuating or venting the products (e.g. steam, tissue debris, tissue fluid, saline, blood, plasma, gases, etc.) generated during a procedure; applying suction to collapse an anatomical region around the antenna 104. Suction may be applied in the uterine cavity to increase the contact of antenna 104 with the uterine endometrium. When a gas such as carbon dioxide is used for distending an anatomical region and/or for detecting perforation of an anatomical region, the gas may be delivered at a pressure between 20-200 mm Hg. In one embodiment, a fluid inserted into a bodily cavity that alters the local environment around cannula 102 and/or working device 104. In one such embodiment, a fluid (e.g. a liquid or gas) is introduced around one or more regions of working device 104 comprising a microwave or radiofrequency antenna. The fluid environment may alter (e.g. improve or worsen) the matching between the antenna and the surrounding target material. The level and/or the change in the microwave returned power with the amount of alteration of the local environment around antenna 104 may be measured and used to take further decisions. Examples of distension media include, but are not limited to: gases such as carbon dioxide and nitrogen; ionic liquids such as saline solutions, lactate solutions, dextrose/dextran solutions; and non-ionic liquids such as solutions of one or more of: sorbitol, glycine and mannitol. The distension medium may have a greater viscosity than that of water to reduce the leakage rate. The distension medium may be introduced in the anatomy through any of the fluid or device transport paths disclosed herein.

In one embodiment of a perforation detection test to rule out procedure related or naturally-present perforations of the uterus, a fluid is introduced into the uterine cavity and leakage of fluid from the uterine cavity is measured or detected. The leakage may be detected by one or more methods including, but not limited to: sensing flow, sensing pressure change, sensing volume change, sensing change in a size or shape parameter of the cavity, and sensing change in the distension of the cavity.

FIGS. 3A-3D show one embodiment of introducing a medical device through a low profile access path created by cannula 102. In this embodiment, an endometrial ablation device 104 is used only as an example of a device that can be introduced through cannula 102. In the embodiment shown, device 104 is an endometrial ablation devices disclosed in US Patent Application Publication numbers 2010/0121319, US 2010/0137857, 2014/0190960 and related applications, the entire disclosures of which are incorporated herein by reference. Other devices disclosed in the above-mentioned patent applications and other elongate devices may similarly be used in the present invention. Distal end of device 104 comprises an antenna 106. An elongate folding member 110 is slidably positioned on the shaft 112 of device 104. Folding member 110 comprises a lumen with a size larger than the size of the shaft 112 and the size of folded antenna 106. The proximal end of folding member 110 may be enlarged or flared. The proximal end of device 104 comprises a connector 114 to connect device 104 to a source of energy. In step shown in FIG. 3A, device 104 is brought adjacent to cannula 102. The distal end of cannula 102 is already positioned at a desired location using any of the methods disclosed herein. Thereafter, in the step shown in FIG. 3B, folding member 110 is advanced distally to cover antenna 106. When folding member 110 passes over antenna 106, antenna 106 is forcibly converted into a low profile collapsed configuration from a larger profile deployed configuration shown in FIG. 3A. This allows the distal end of device 104 to be introduced into the low profile access path of cannula 102. In the step shown in FIG. 3C, the distal end of device 104 is pushed into the proximal end of cannula 102. In the step shown in FIG. 3D, device 104 is pushed distally through cannula 102 such that antenna 106 emerges out of the distal end of cannula 102 into the desired target region. Antenna 106 is converted into the deployed configuration and is located at the desired position already defined by the distal end of cannula 102. In one embodiment, the outer dimension of folding member 110 is smaller than the dimension of the lumen of cannula 102 at the proximal region of cannula 102. This allows insertion of folding member 110 into the proximal end of cannula 102. In one particular embodiment, dimension of cannula 102 lumen distal to the proximal region of cannula 102 is smaller than the dimension of cannula 102 lumen at the proximal region of cannula 102. This limits further insertion of folding member 110 beyond the proximal region of cannula 102. In one embodiment, elongate folding member 110 is made of one or more biocompatible materials include, but not limited to: metals, polymers (including, but not limited to: PEBAX, Teflon, polyethylene, and polypropylene), glass, and ceramics. Folding member 110 allows the easier introduction of foldable elements through small lumen, minimally invasive openings.

In another embodiment, antenna 106 or other functional elements located on working device 104 are pinched or otherwise compressed by a user's fingers to bring them into a collapsed, low profile configuration. Thereafter, the user holds the antenna 106 or other functional elements in the low profile configuration and pushed them into cannula 102.

Figure 4A:
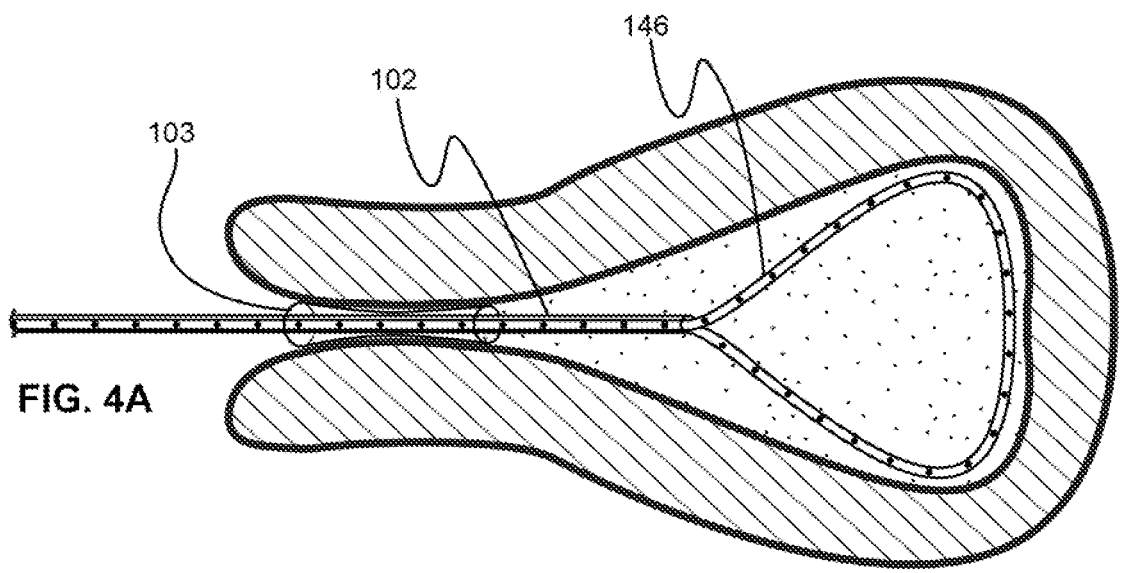
FIGS. 4A-4H show various embodiments of methods and devices to evacuate fluids from an anatomical region.

FIGS. 4A-4H show various embodiments of methods and devices to evacuate fluids from an anatomical region. FIG. 4A shows an embodiment of a fluid evacuation device 146 comprising a flexible, elongate, hollow tubular region comprising one or more perforations or openings communicating with a lumen of device 146. In the embodiment shown, device 146 is introduced in a looped configuration in the anatomy and the size of the loop is increased or reduced by a user to enable device 146 to come into contact with the desired portions of the anatomy. A vacuum is applied to the lumen of device 146 that evacuates fluid from the anatomy. In one embodiment, device 146 is inserted into the uterine cavity and is used to evacuate fluids from areas of the uterine cavity including, but not limited to: regions near the cornua, mid fundus region, mid uterine region, and lower uterine region.

Figure 4B:
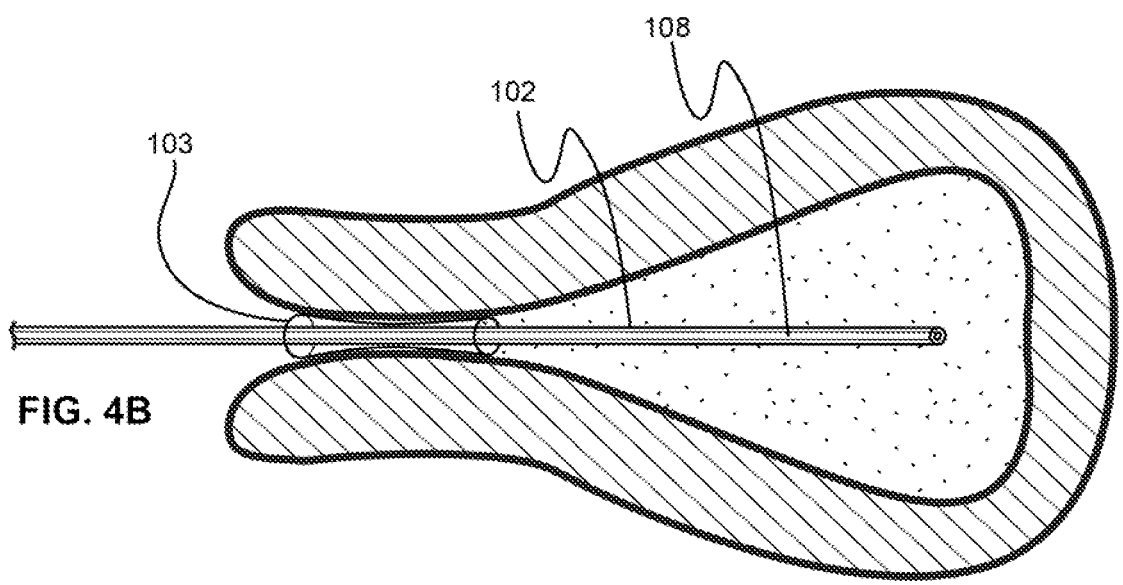
Figure 4C:
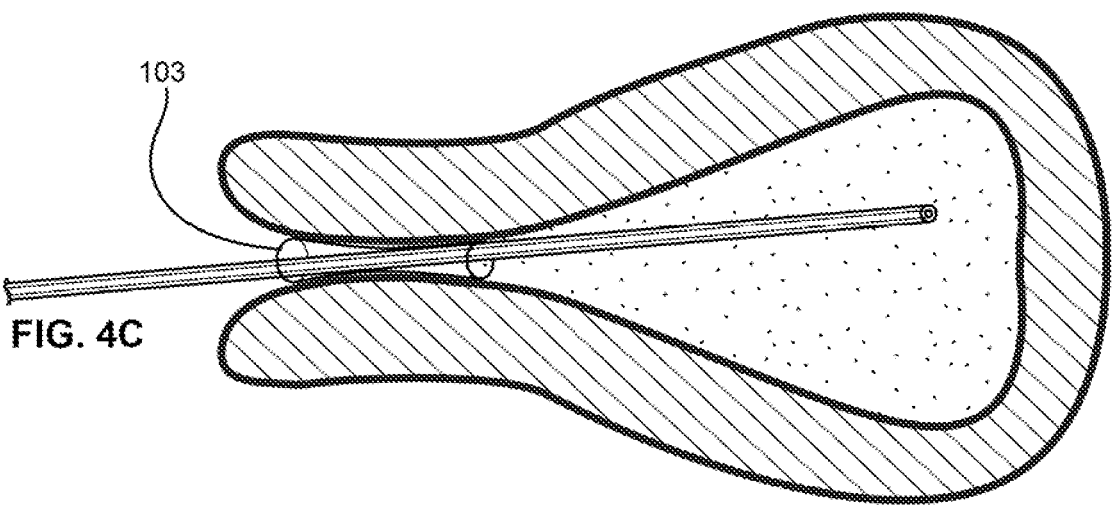

FIGS. 4B and 4C shows the steps of a method of using a combination of cannula 102 and tube 108 to evacuate fluids from the anatomy. In this embodiment, the access channel comprises a flexible cannula 102 and a stiffening member comprising a rigid or semi-rigid tube 108 located within a lumen of the cannula 102. The tube 108 is stiffer than cannula 102 and increases the stiffness of the assembly. This allows a user to move the distal end of cannula 102 to and evacuate fluids from various parts of the anatomy as shown in FIG. 4C. This allows the user to evacuate fluids as disclosed elsewhere in this specification. In alternate embodiments, fluid evacuation is done using cannula 102 or a combination of cannula 102 and endoscope 100.

Figure 4D:
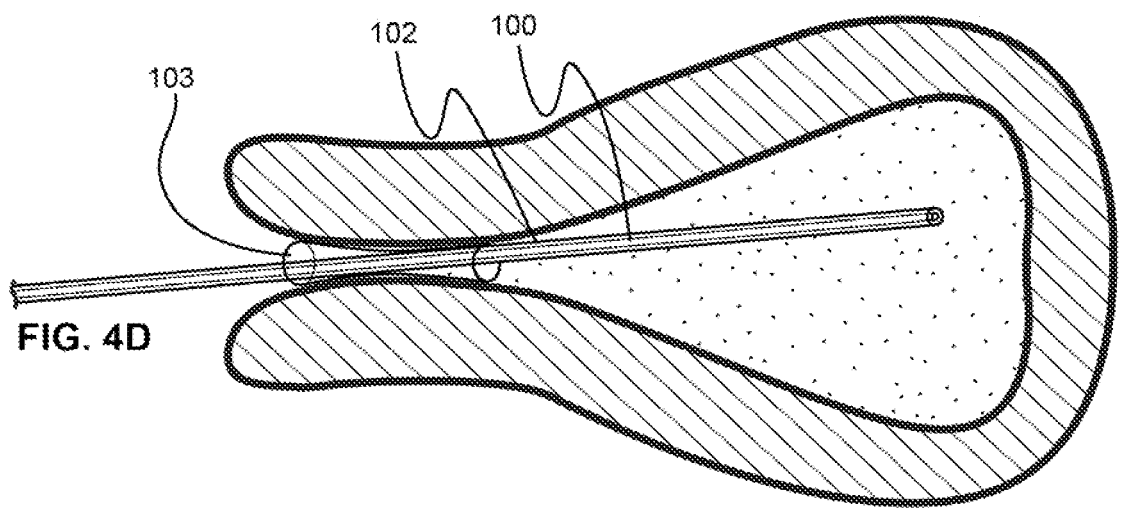

FIG. 4D shows a method of using a combination of cannula 102, endoscope 100, and tube 108 to evacuate fluids from the anatomy. This method has the advantage that the combination can be moved to various regions of the anatomy and endoscope 100 can be used to visualize pockets of fluids in the anatomy for targeted evacuation of fluids.

Figure 4E:
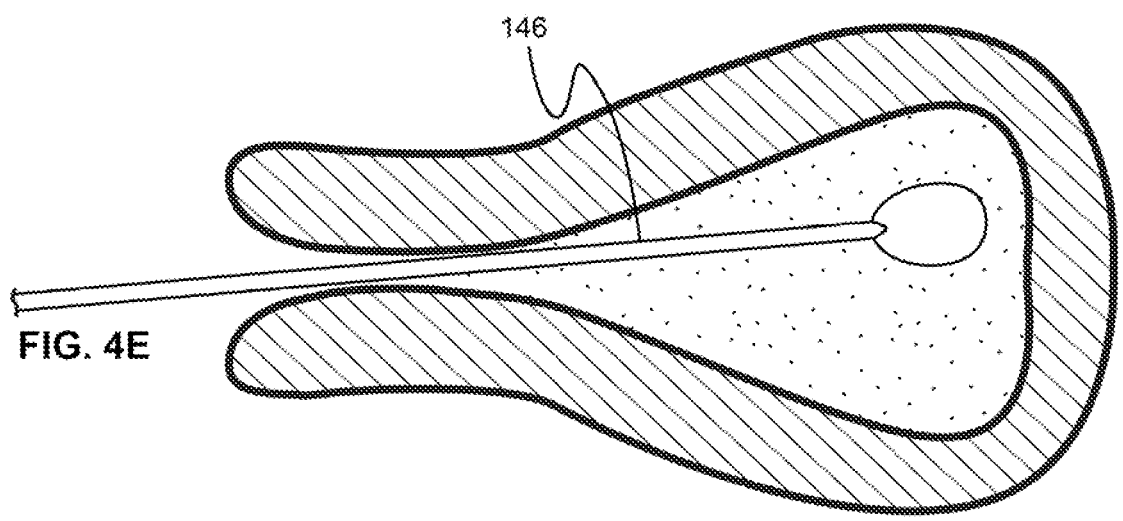
Figure 4F:
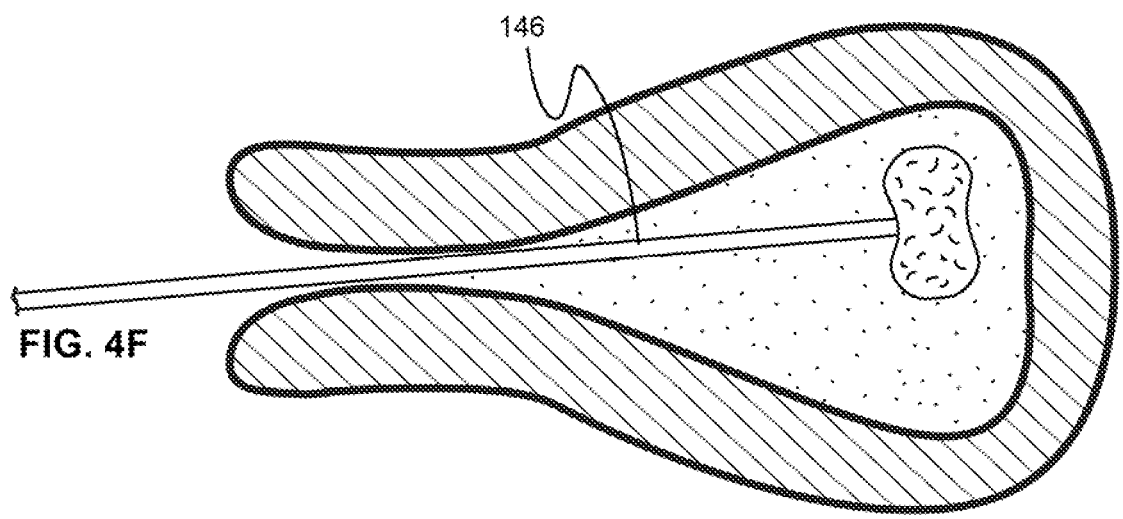

FIGS. 4E and 4F shows embodiments of fluid evacuation devices 146 comprising a scoop and a sponge respectively at the distal region of the devices 146. A scoop is defined as a concave surface capable of scooping out a fluid. The devices disclosed in FIGS. 4E and 4F may have a fluid evacuation lumen in communication with the scoop and the sponge respectively. Alternately, the fluid can be evacuated by one or more passes with the scoop or the sponge with the fluid stored in the scoop or the sponge itself.

Figure 4G:
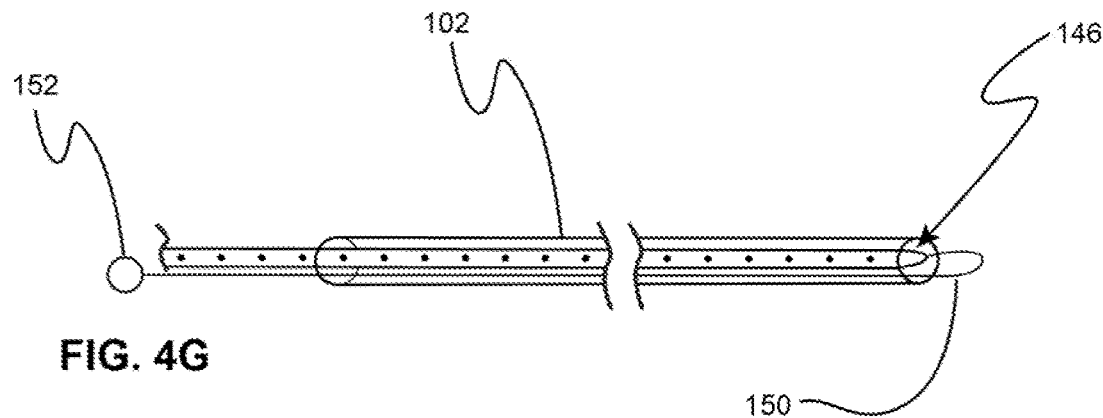
Figure 4H:
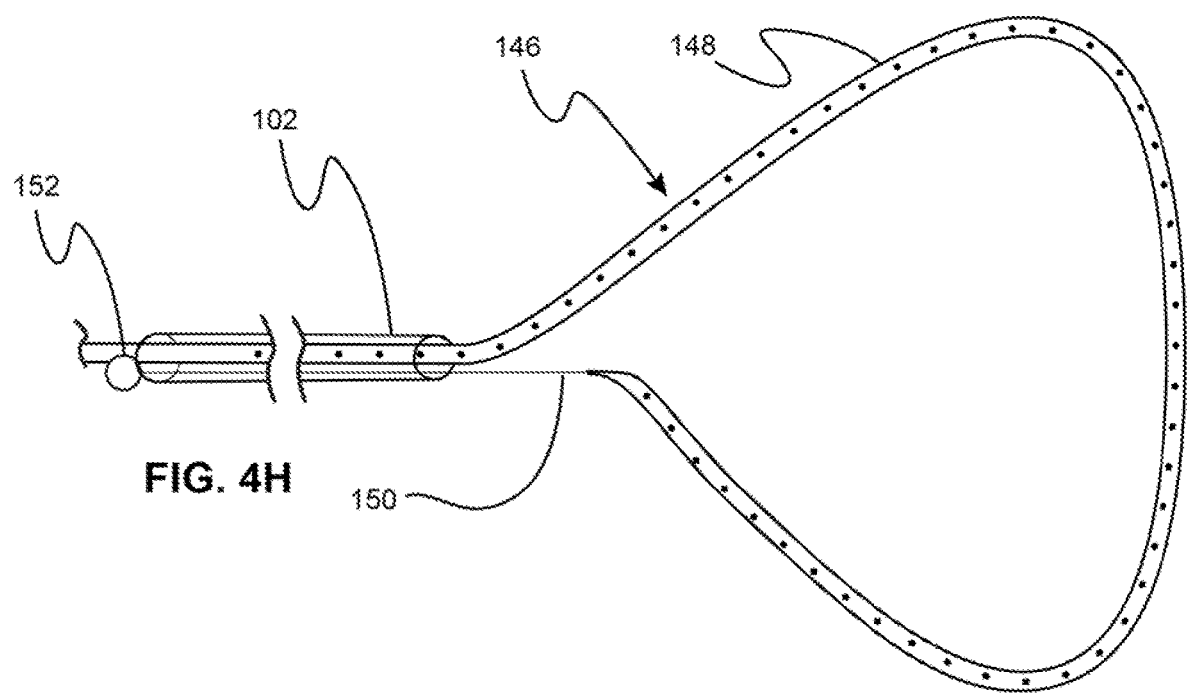

FIGS. 4G and 4H show the insertion configuration and the working configuration respectively of an embodiment of a fluid evacuation device 146. Device 146 comprises an elongate hollow shaft 148 comprising a lumen. The lumen is in fluid communication with or more openings on the surface of shaft 148 as shown. The distal end of shaft 148 is connected to a flexible member 150 that is looped back in the lumen of cannula 102. The proximal end of member 150 terminates in a stopper 152. Stopper 152 restricts the amount of member 150 that can enter cannula 102. In the insertion configuration shown in FIG. 4H, shaft 148 and flexible member 150 are substantially parallel to each other. After inserting device 146 in the anatomy, shaft 148 is pushed distally so that a region of shaft 148 is deployed in the anatomy. Using methods disclosed herein fluids may be evacuated from anatomical locations.

Any of the fluid evacuation methods disclosed herein may be performed after plugging an insertion tract with a plug as shown in FIGS. 4A-4D. Any of the fluid evacuation devices 146 disclosed herein may be introduced through cannula 102 or independently through a tract. Any of the fluid evacuation devices 146 disclosed herein may be used to evacuate one or more fluids from a hollow cavity such as the uterine cavity. Any of the fluid evacuation methods disclosed herein may also be used to introduce instead of evacuate one or more fluids, examples of which are disclosed herein. Fluid evacuation or introduction methods disclosed herein may be performed before, during or after a medical procedure disclosed herein. Any of the fluid evacuation devices disclosed herein may be used to introduce a gas into an anatomical region to force a liquid out of an anatomical region. Any of the fluid evacuation devices 146 disclosed herein may be manipulated in the anatomy by one or more of: advancing or withdrawing, torquing or rotating, bending, steering using a steering modality, or using other techniques disclosed elsewhere in this specification.

Figure 5A:
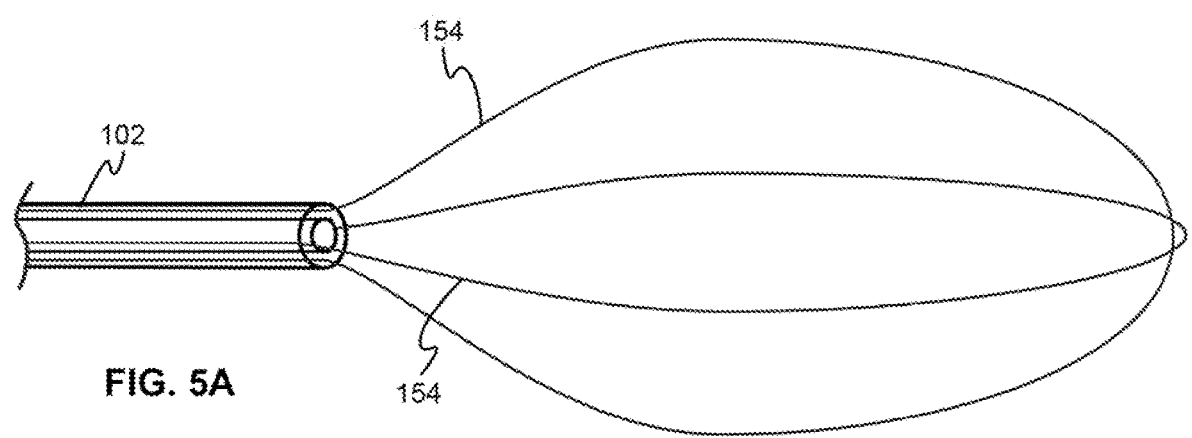
FIG. 5A shows an embodiment of a cannula comprising mechanical distension means.

Any of the methods and devices disclosed herein may be used before, during, or after distending an anatomical region. Several method and device embodiments herein relate to the introduction or withdrawal of fluids from the anatomy. Such devices and methods may be used to distend the anatomy using fluid under a sufficient pressure. The fluid may be a gas or a liquid or combinations thereof. In alternate embodiments, a mechanical means of distension are used to distend the anatomical region with or without fluid based distension. FIG. 5A shows an embodiment of a cannula 102 comprising mechanical distension means. In the embodiment shown, the mechanical distension means are two distending loops 154 that can be expanded and contracted by a user depending on the requirement of a procedure. In one embodiment, distension means 120 are completely or partially withdrawn inside cannula 102 when cannula 102 is inserted into the anatomy. Thereafter, distension means 120 are deployed from cannula 102 after cannula 102 is inserted into the anatomy. In one embodiment, a user engages a control on the proximal region of cannula 102 to change the size of loops 154 as needed. Even though loops 154 are shown perpendicular to each other, other arrangements of loops 154 are possible. Cannula 102 or other devices disclosed herein may have 1-10 distending loops 154. Alternate mechanical means of distension include, but are not limited to one or more deployable or non-deployable loops, balloons, expandable baskets, stents, elongate mechanical arms, etc.

Any of the endoscopes 100 herein may be a rigid endoscope, a flexible endoscope (e.g. a flexible hysteroscope) or a low profile mini-endoscope (e.g. a mini hysteroscope). The view angle of vision of the endoscope may range from 0 degrees to 80 degrees. Any of the endoscopes 100 or other devices disclosed herein may comprise one or more steering mechanisms disclosed herein. Any of the endoscopes 100 herein may be used to image the anatomy in 3D.

In any of the embodiments herein, a camera may be used to visualize the anatomy. In one embodiment, the camera is a light sensing camera. The camera may be located on endoscope 100 (e.g. on the distal tip) or in any device disclosed herein. The camera may be outside the anatomy. For example, endoscope 100 may comprise light transmission elements that are optically coupled to a camera outside the anatomy. The camera may be a CCD or CMOS based camera. Multiple endoscopes 100 or multiple cameras may be used to perform one or more of: image multiple regions of the anatomy simultaneously, obtain three dimensional images of the anatomy, and image a region of the anatomy and a region of the device simultaneously. The camera can be optically or electronically coupled to a viewing means.

The light source in any of the embodiments disclosed herein may be a multi-spectral light source or a monochromatic light source. The distal region of any of the devices disclosed herein may comprise a diffuser to diffuse light from a light source. In one embodiment, the source of light is within an endoscope 100. In another embodiment, the source of light is separate from endoscope 100. Light may be delivered to the anatomy by one or more light paths or channels. The field of view of endoscopes 100 disclosed herein may range up to 120 degrees. The light source may be integral to the wall of cannula 102 (e.g. as shown in FIG. 4A) or endoscope 100 or device 104. The light source may comprise plastic or polymeric or glass fibers doped with additional elements such as fluorescent or scintillating fibers. The light source may be synchronized with the light detection from the endoscope 100. The light source may illuminate a region with a solid angle ranging from 10 degrees to 340 degrees. The light source may be integral to a wall of any of the devices disclosed herein. The light paths of the illumination and the reflected light from the anatomy may be same or different.

Figure 6A:
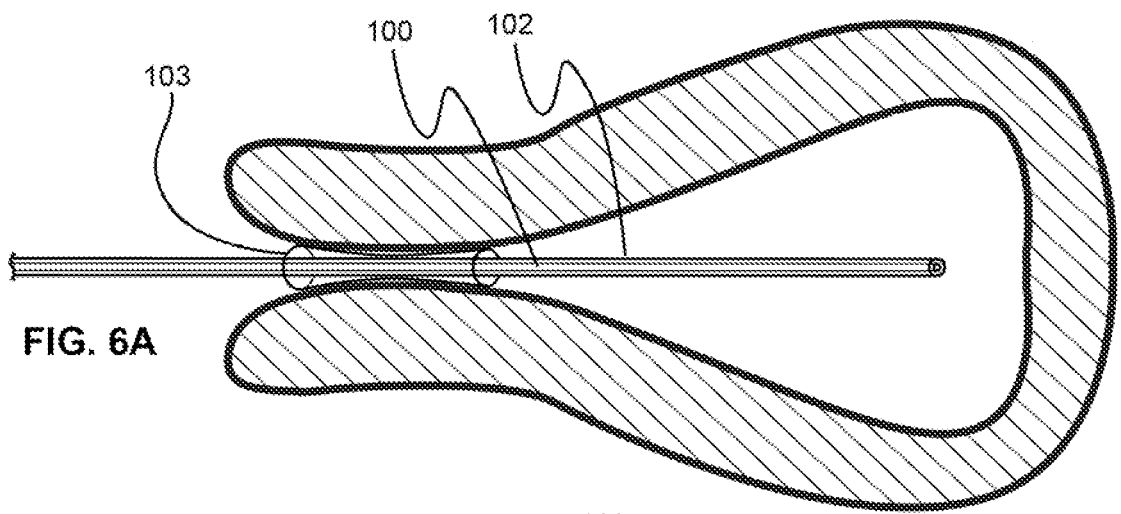
FIGS. 6A-6C show the steps of inserting and deploying a balloon based device using the method disclosed herein.
Figure 6B:
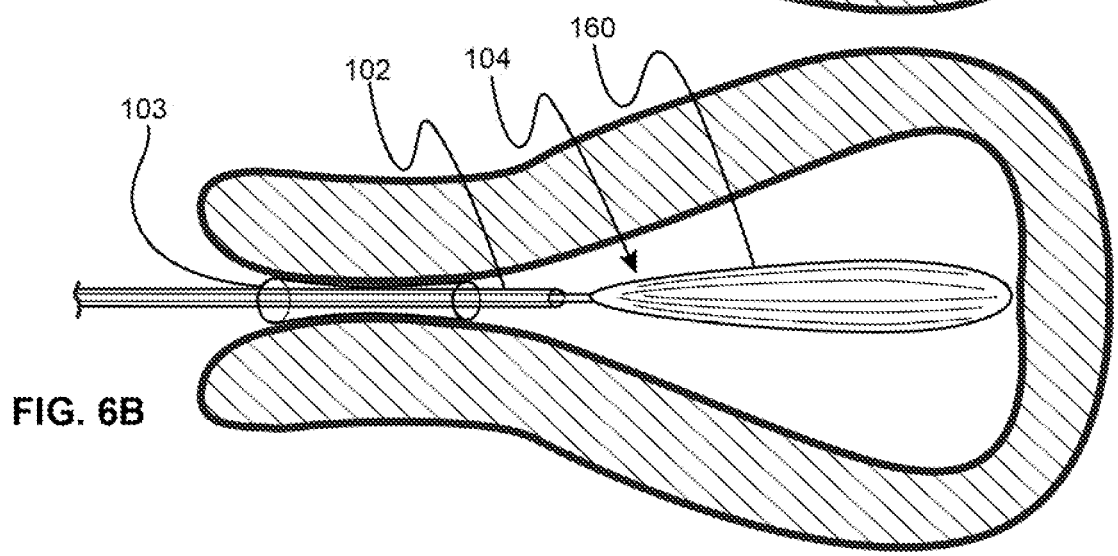
Figure 6C:
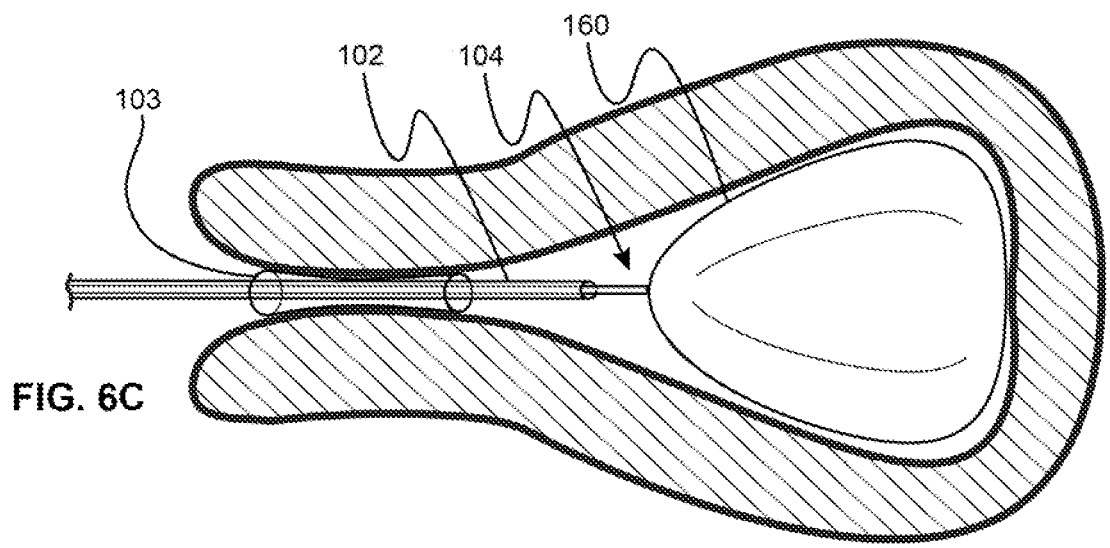

FIGS. 6A-6C show the steps of inserting and deploying a balloon based device using the method disclosed herein. In FIG. 6A, cannula 102 and endoscope 100 are introduced into an anatomical region and navigated under endoscopic guidance such that the distal end of cannula 102 is placed in a desired location. Thereafter, endoscope 100 is removed from cannula. This step may be performed using any of the methods disclosed herein. Thereafter, in FIG. 6B, a working device 104 (e.g. a working device 104 comprising a balloon 160) is introduced through cannula 102 into the anatomical region. Thereafter, in FIG. 6C, working device 104 is converted to a working configuration from an insertion configuration and is used to perform a medical procedure in the anatomical region.

Figure 6D:
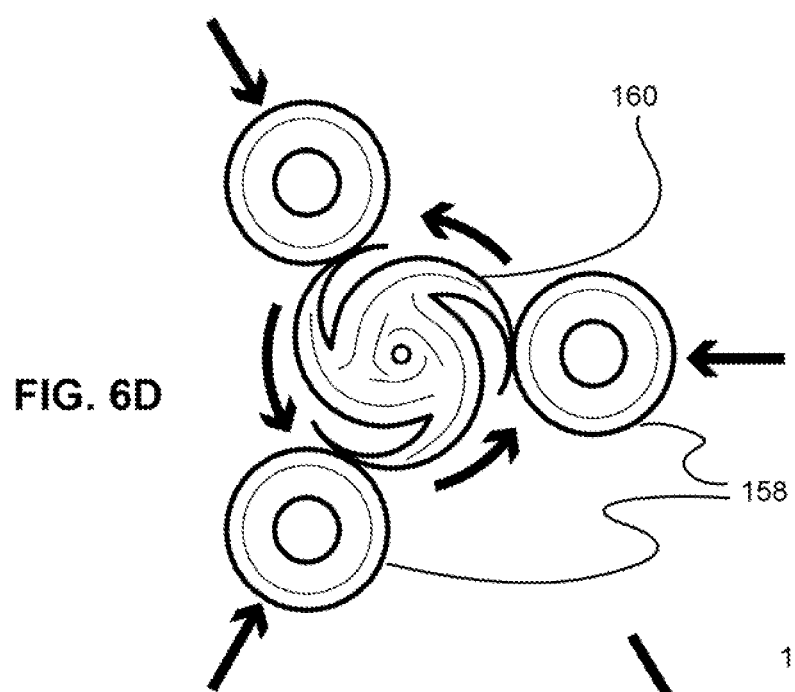
FIGS. 6D-6F show the steps of converting a balloon to a low profile insertion configuration.
Figure 6E:
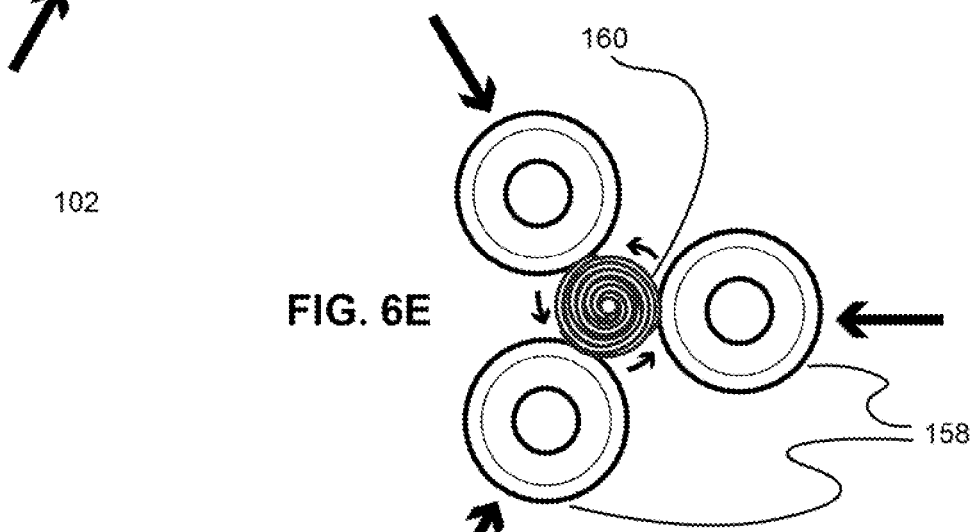
Figure 6F:
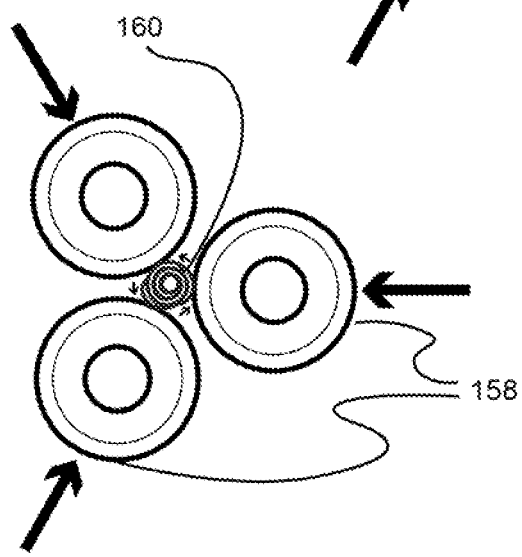

FIGS. 6D-6F show the steps of converting a balloon to a low profile insertion configuration. Similar methods may be used to fold or otherwise convert any of the devices disclosed herein into a lower profile configuration. In this specification, lower profile is defined as having one smaller transverse (at right angles to the long axis of the body) dimension. In FIG. 6D, three pinching members 158 are used to pinch or otherwise squeeze a balloon 160. Balloon 160 is rotated by a user as it is being pinched by pinching members 158. This creates one or more folds of the balloon material as shown in FIG. 6D. This process is continued as shown in FIGS. 6E and 6F to create a folded, low profile balloon 160. In one embodiment, pinching members 158 are elongate mechanical members located on a separate device. In one embodiment, pinching members 158 are a user's fingers. Two to 10 pinching members may be used similarly to fold balloon 160 or other devices disclosed herein. Balloon 160 may be located on a working device 104 or any other device disclosed herein.

In alternate embodiments, balloon 160 is folded by one or more of: inserting balloon 160 into a tapered lumen, inserting balloon 160 into a small diameter lumen, using a folding member 110 as shown in FIGS. 3A-3D, using a lumen of cannula 102, compressing balloon 160 using a compressing device, and drawing a vacuum to collapse balloon 160.

Figure 7A:
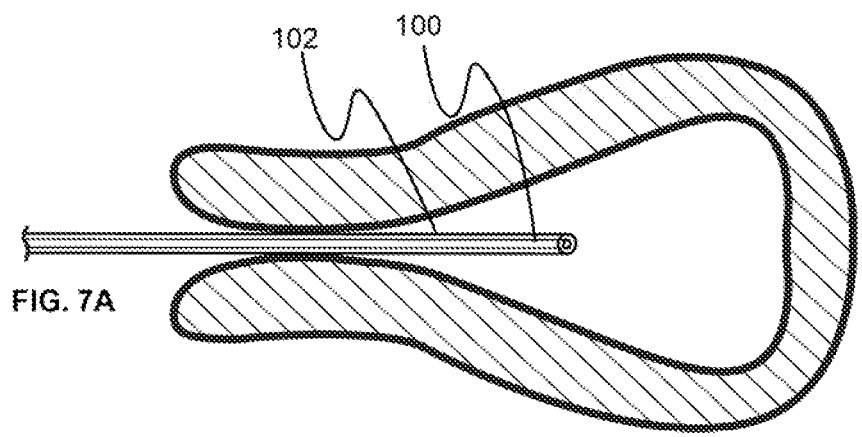
FIGS. 7A-7D show the steps of a method of using a guidewire or other non-lumen based device as an access channel into an anatomical region.
Figure 7B:
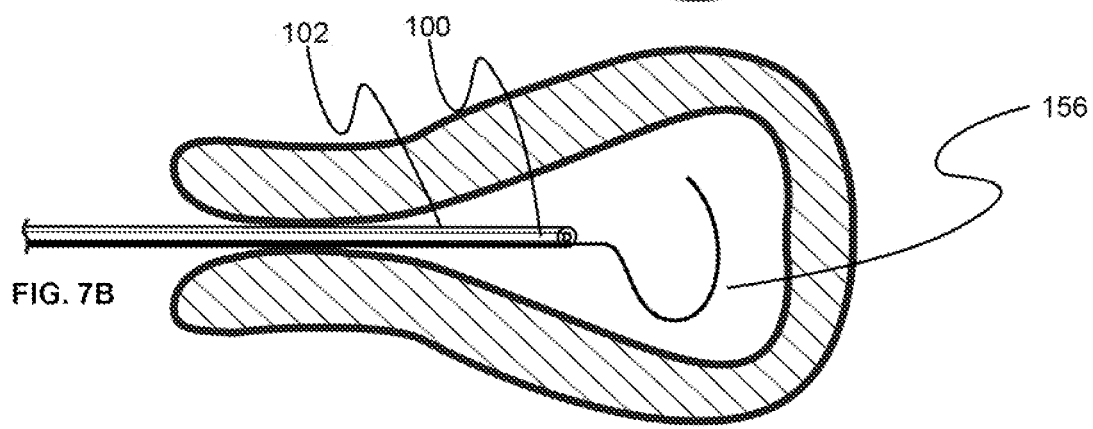
Figure 7C:
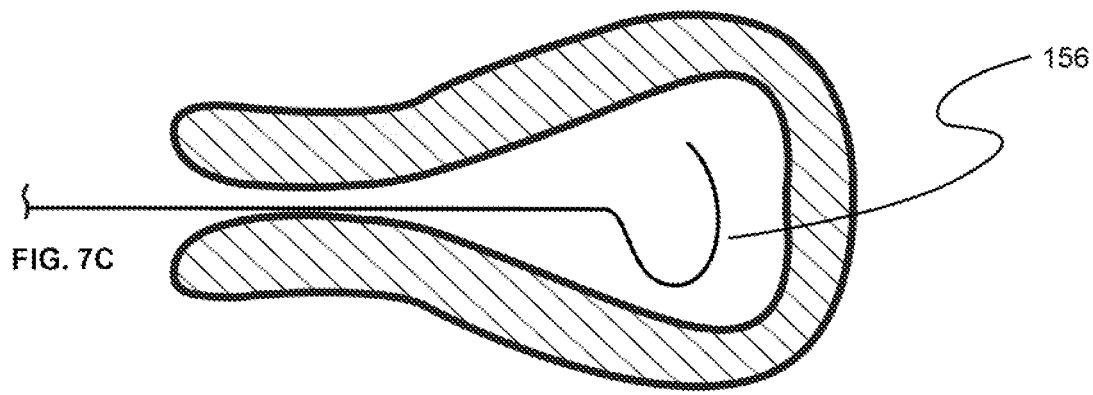
Figure 7D:
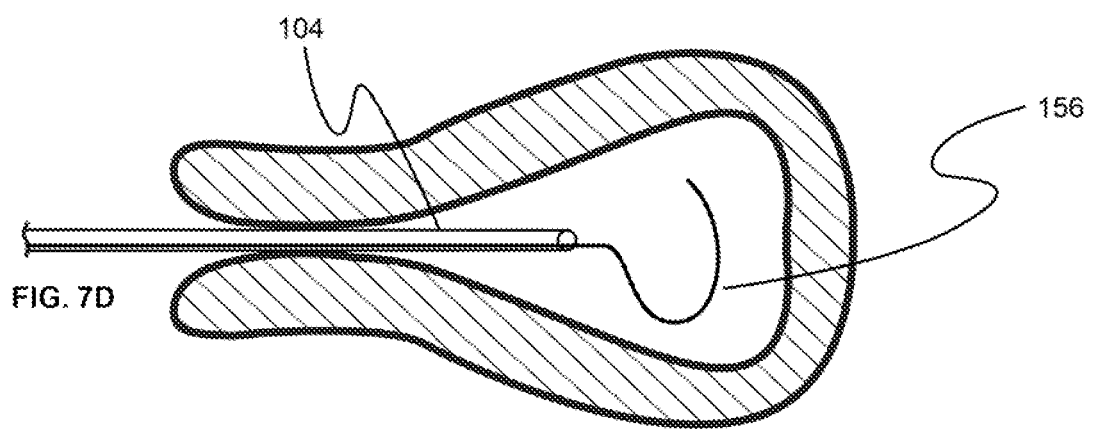

FIGS. 7A-7D show the steps of a method of using a guidewire or other non-lumen based device as an access channel into an anatomical region. In FIG. 7A, cannula 102 and endoscope 100 are introduced into an anatomical region using any of the methods disclosed herein. Thereafter, cannula 102 and endoscope 100 are navigated to a desired location in the anatomical region under endoscopic guidance. In any of the embodiments disclosed herein, cannula 102 may act as a sheath for endoscope 100. In such embodiments, a space between cannula 102 and endoscope 100 is used to introduce to or withdraw fluids from an anatomical region as described elsewhere in this specification. In FIG. 7B, a guidewire 156 is introduced through a lumen of the combination of cannula 102 and endoscope 100. Thereafter, cannula 102 and endoscope 100 are removed leaving guidewire 156 behind as shown in FIG. 7C. This creates an access channel into the anatomical region. In FIG. 7C, a working device 104 is introduced in the anatomical region over guidewire 156 and is used to perform a medical procedure.

Figure 8A:
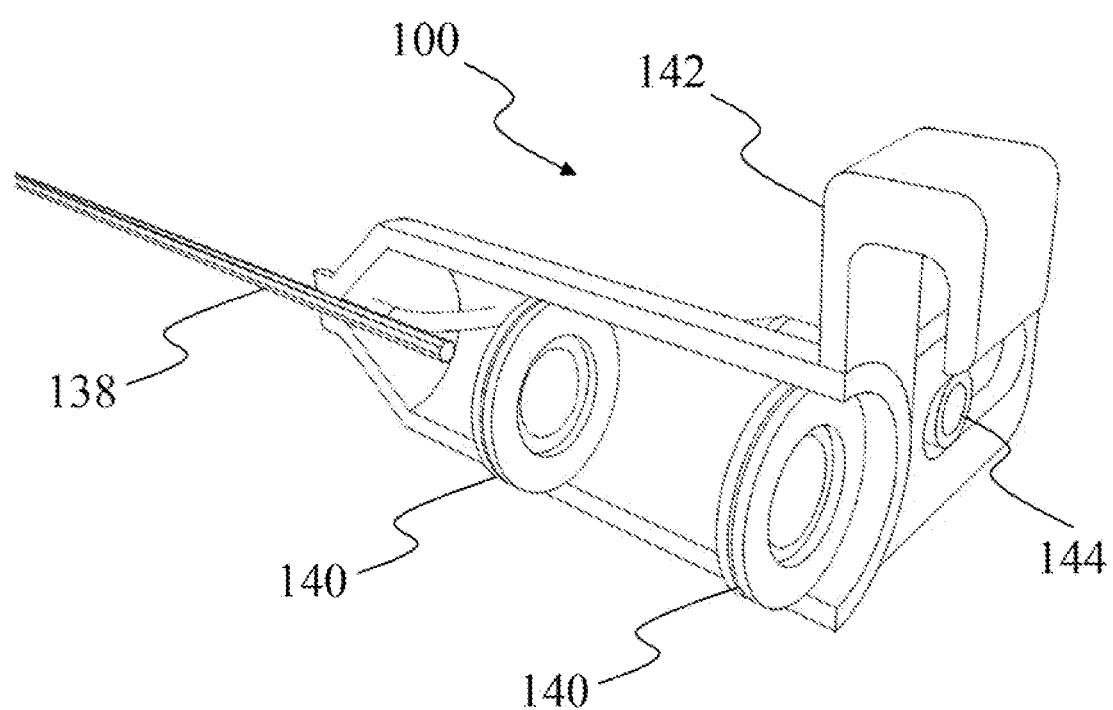
FIG. 8A shows an embodiment of an endoscope that may be used with any of the device and method embodiments disclosed herein.
Figure 8B:
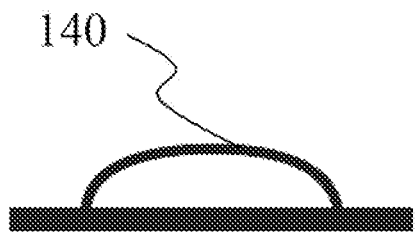
FIGS. 8B-8F show alternate embodiments of lenses that can be used in any of the embodiments disclosed herein.
Figure 8C:
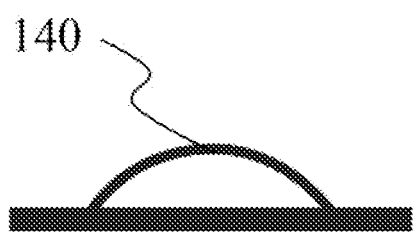
Figure 8D:
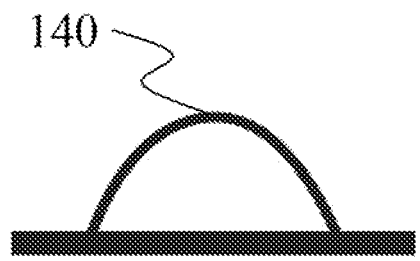
Figure 8E:
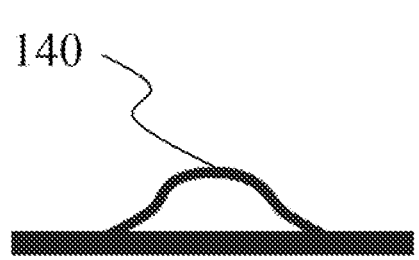
Figure 8F:
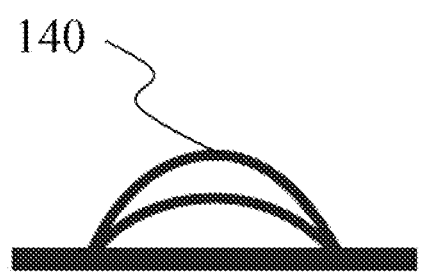

FIG. 8A shows an embodiment of an endoscope 100 that may be used with any of the device and method embodiments disclosed herein. Endoscope 100 comprises a fiberoptic bundle 138 that comprises one to 15,000 fiberoptic fibers. Examples of fiberoptic fibers include, but are not limited to: glass optical fibers (made from materials such as silica, fluorozirconate, fluoroaluminate, chalcogenide glasses, crystalline materials like sapphire) and plastic optical fibers (made from materials such as PMMA/acrylic, fluorinated polymers, perfluorinated polymers). Fiberoptic bundles 138 may comprise rigid, semi-rigid or flexible fibers. The fibers may be multi-mode fibers (MMF) or single-mode fibers (SMF). Endoscope 100 may further comprise one or more optical lenses 140. Lens 140 may be mounted on a casing of endoscope 100 to focus light coming from fiberoptic bundle 138 or other light channels. Endoscope 100 may comprise between zero to five lenses 140. Lens 140 may be constructed of one or more materials selected from the group including, but not limited to: glass, Liquid Silicone Rubber, ceramics, and polymers (e.g. PMMA). Lens 140 may be mounted in an adjustable casing to focus on fiberoptic bundle 138 or other light channels at variable camera zoom lengths. Endoscope 100 further comprises a camera mount 142 or other mechanical attachment to hold an external camera in optical communication with the fiberoptic bundle 138 or other light channels. The external camera may be located on one of: an endoscope connector, a cell phone display, and a stand-alone display. In one embodiment, endoscope 100 further comprises a light source adapter 144 to enable an external light source to optically communicate with fiberoptic bundle 138 or other light channels. The light source adapter 144 may be adjustable to adjust to the position of the external light source. As discussed elsewhere in this specification, a portion of fibers of fiberoptic bundle 138 may be adapted to transmit light into a anatomy and the remainder of the fibers may be adapted to gather light from the anatomy and into a camera or other image capturing mechanism. The illumination fibers and the image capturing fibers may be oriented relative to each other in a variety of orientations. In one embodiment, the illumination fibers and the image capturing fibers are oriented side-by-side. In an alternate embodiment, the illumination fibers form a ring around the image capturing fibers. In another alternate embodiment, one to eight illumination fibers are arranged along multiple image capturing fibers. In one embodiment, the external light source is a high intensity halogen and xenon based light source.

FIGS. 8B-8F show alternate embodiments of lens 140 that can be used in any of the embodiments disclosed herein. In one embodiment of constructing a lens 140 of optical grade Liquid Silicone Rubber (LSR), a base lens surface is cast onto a polished surface and cured. Thereafter, an additional amount of LSR is placed in the center of the cured lens base. Thereafter, the lens base is inverted and cured a second time. This process may be repeated for variability of lens effects. One advantage of this process is that dependence on mold surface quality is greatly reduced. In an alternate embodiment, a lens 140 made of LSR is cast in molds.

Any of the lenses 140 disclosed herein may be one of: rod lens, bead lens, balls lens, and graded index (GRIN) lenses. The lenses may operate at a view angle ranging from zero degrees to 45 degrees.

Figure 9A:
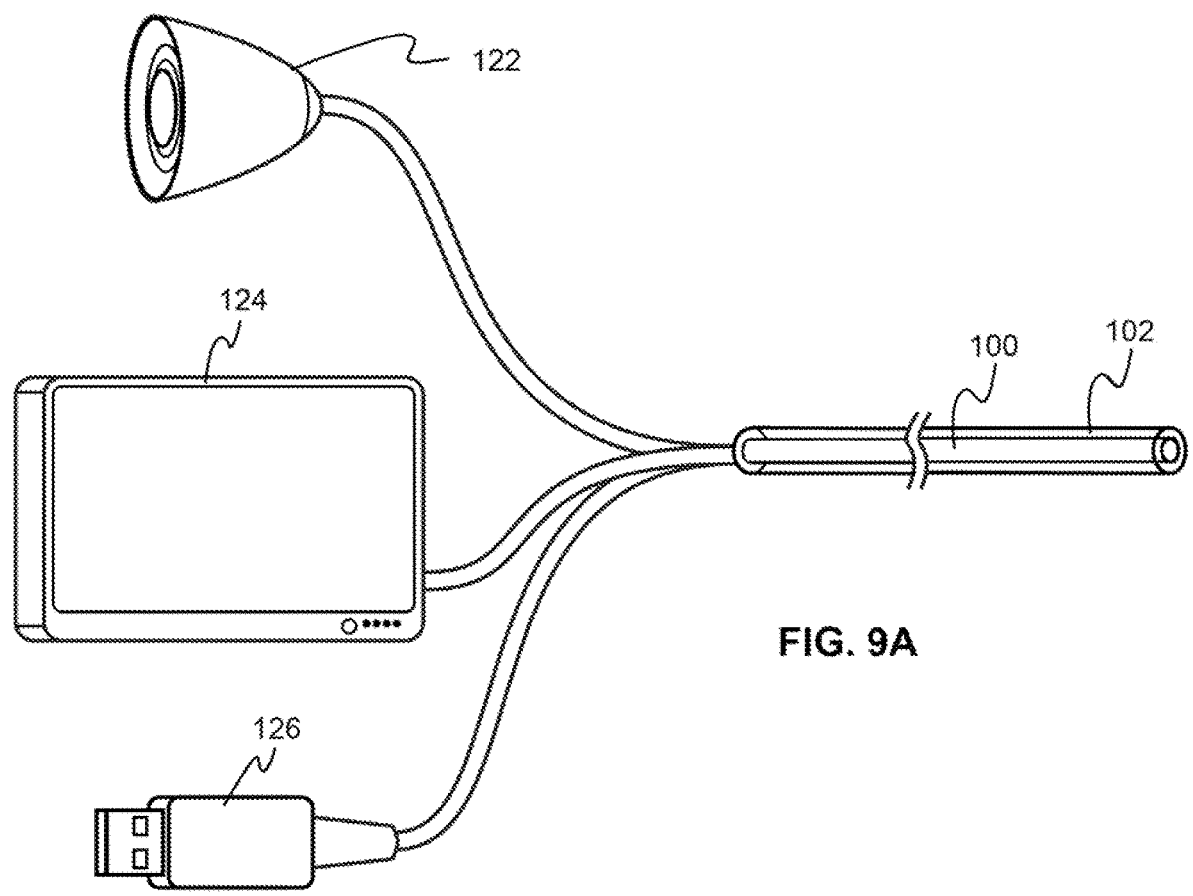
FIG. 9A shows an embodiment of the combination of a cannula and an endoscope comprising various alternate means of transmitting imaging information to a user.

FIG. 9A shows an embodiment of the combination of cannula 102 and endoscope 100 comprising various alternate means of transmitting imaging information to a user. In one embodiment, an eyepiece 122 is located at or near a proximal region of cannula 102. The user can look into the eyepiece directly or through a camera to view the endoscopic images. In one embodiment, a display 124 is located at or near a proximal region of cannula 102. The user can look into the display to view the endoscopic images. The display may be located as a separate unit or may be connected to one of the components of a system such as cannula 102, endoscope 100 or device 104. In one such embodiment, display 124 is the display of a smartphone. In one embodiment, a data output port 126 is located at or near a proximal region of cannula 102. The user can connect the data output port 126 to a suitable display to view the endoscopic images. Any of the displays herein may be located on a phone or may be a standalone display. Any of the displays herein may be used to display photos and/or videos obtained from endoscope 100. Any of the displays herein may have an annotation and/or measurement capability for the user to anoint and/or measure data on endoscopic photos or videos. Any of the displays herein may be connected to a recording system to record endoscopic or other data. In one such embodiment, the data is recorded on the display itself. In another such embodiment, the data is recorded on a smartphone. Although a physical port 126 is shown, any of the embodiments herein may comprise a wireless transmission capability to wirelessly transmit data endoscopic or other data obtained during a procedure. In one such embodiment, endoscope 100 is a wire-free endoscope such as the Pillcam® made by Given Imaging Ltd.

In another embodiment, a hysteroscope is inserted into the uterine cavity and is used to perform one or more of the diagnostic procedures disclosed herein. Thereafter, the hysteroscope and its accessories (if any) are removed from the uterine cavity. Thereafter, a diagnostic or therapeutic device is inserted into the uterine cavity to perform a diagnostic or therapeutic procedure based on the feedback obtained from the hysteroscope guided diagnostic procedure.

In alternate embodiments, instead of or in addition to a hysteroscope, other diagnostic modalities may be used. In one such embodiment, infrared (IR) imaging or other IR measurement is used to determine the temperature at one or more regions of a device or tissue. For example, an IR camera may be located outside the tissue cavity that is being diagnosed or treated. This camera may be used to measure the temperature at one or more regions to determine e.g. the end of therapeutic energy delivery. In another example, a waveguide or other transmitter of IR signals is inserted within the hollow cavity or outside the hollow cavity or within the walls of the hollow cavity. The IR signals may be used for temperature measurement. In another embodiment, a Fiberoptic probes (e.g. those made by Luxtron) or other temperature measurement probes may be used to measure the temperature at one or more regions of the device or tissue. The temperature may be measured at one or more spots or regions of the tissue or device or may be used to take a more "global" measurement of a larger region such as an entire anatomical cavity e.g. a uterine cavity.

Another example of a diagnostic modality is near infrared imaging (e.g. VeinViewer® like modalities) to visualize blood vessels and blood patterns.

Another example of a diagnostic modality is ultrasound imaging during one or more steps of a procedure. Ultrasound imaging may be used for one or more steps including, but not limited to: determining the position of one or more regions of a device, determining deployment and/or proper functioning of a working element 106, determining the placement of one or more regions of a device (e.g. determine that the distal end of a working device 104 is at the fundus), visualizing the deployment of working element 106, determining the size and/or shape of one or more regions of the anatomy, determining the treatment settings to be used (e.g. patient customized energy delivery settings for a thermal procedure based on anatomical measurements), obtaining feedback on the performance and/or safety of a treatment (e.g. determining the depth and coverage of an ablation), and determining presence of a pathology (e.g. extent and location of adenomyosis). The ultrasound probe may be located outside the body (e.g. transabdominal, transthoracic, etc.) or may be located within a body passage or lumen (e.g. transvaginal, transrectal, etc). One or more positive or negative contrast agents may be used.

More examples of diagnostic modalities are radiological modalities such as CT, MRI, or X-ray/fluoroscopy which can be used during one or more steps of a procedure. They may be used for one or more steps including, but not limited to: determining the position of one or more regions of a device, determining the placement of one or more regions of a device (e.g. determine that the distal end of a working device 104 is at the fundus), visualizing the deployment of working element 106, determining the size and/or shape of one or more regions of the anatomy, determining the treatment settings to be used (e.g. patient customized energy delivery settings for a thermal procedure based on anatomical measurements), obtaining feedback on the performance and/or safety of a treatment (e.g. determining the depth and coverage of an ablation or other lesions), and determining presence of a pathology (e.g. extent and location of adenomyosis). One or more positive or negative contrast agents may be used.

Any of the embodiments herein may use a microwave detector to detect the presence and/or the intensity of microwave signals. In one embodiment, a microwave detector is present outside the target tissue or cavity. In another embodiment, the microwave detector is present within the target tissue or cavity. Examples of microwave detectors include, but are not limited to: diodes e.g. tunnel diodes, Schottky diodes, and planar-doped barrier diode.

Any of the embodiments herein may use a radiometric microwave thermometer comprising a microwave sensor and electronic means for processing the electrical signal delivered by the sensor. One example of such a thermometer is disclosed in US 2010-0061421, the entire disclosure of which is incorporated herein by reference.

Even though a large section of the disclosure deals with an endoscope 100 or other imaging device introduced through the same insertion path as working device 104, in alternate embodiments, endoscope 100 or other imaging device may be introduced through alternate insertion paths such as a path outside the target tissue. The endoscope 100 or other imaging device may be inserted through a natural lumen or through artificially created openings or channels on the body such as laparoscopic or other endoscopic openings or channels.

Even though endometrial ablation devices are used as an example of a working device 104, it should be noted that a variety of other diagnostic, therapeutic, or preventative devices may be used in the invention disclosed herein. Examples of such devices include, but are not limited to devices comprising: radiofrequency electrodes including radiofrequency ablation electrodes, heating elements, cryotherapy elements, elements for emitting laser and other radiation, elements for introducing one or more fluids, diagnostic modalities including, but are not limited to: temperature sensors, impedance sensors, electrophysiological signal sensors, and visualization elements. Any working elements 106 disclosed herein may be conformable to acquire the shape of a portion of the anatomical region or otherwise be shaped by one or more portions of the anatomical region. For example, a working element 106 disclosed herein may be elastically flexible to conform to the shape of a small cavity or to the shape of an adjacent wall of the cavity into which working element 106 is deployed. Working elements 106 disclosed herein may be sized and shaped to approximate the size and shape of the target anatomy such as the uterine cavity.

Any of the devices disclosed herein may have variable stiffness along their length. In one such embodiment, a distal region of a device is softer than a proximal region. The cross-section of any of the devices disclosed herein may be non-circular. Any of the devices disclosed herein may comprise one or more pre-shaped regions. Any of the devices disclosed herein may comprise steering or navigating modalities.

Several embodiments of slim and flexible devices and access channels are disclosed herein. This allows the user to introduce devices and/or fluids minimally invasively through small incisions or openings or even non-invasively through natural openings or passageways. Even though a large section of the disclosure deals with access channels created to the uterus, it should be noted that a variety of diagnostic, therapeutic, or preventative procedures may be performed using the invention disclosed herein while creating access channels to other organs, cavities, or other hollow bodily regions. Examples of such access channels include, but are not limited to: percutaneous access into or through the vasculature, access channels from the anus, mouth or nostrils into the gastro-intestinal tract, access channels from the vagina into the female reproductive system, access channels from the urethra into the urinary system, access channels from the ear, nostrils or mouth into the ENT system, etc. The devices and methods disclosed herein may be used to ablate diseased tissue or healthy tissue or unwanted tissue in organs or artificially created cavities. The devices disclosed herein may be introduced through laparoscopic, thoracoscopic, cystoscopic, hysteroscopic or other endoscopic openings or instrumentation into or near organs or bodily cavities. The methods disclosed herein may be performed under real-time monitoring e.g. by using one or more of: direct visual observation, hysteroscopy, cystoscopy, endoscopy, laparoscopy, ultrasound imaging, radiological imaging, etc.

Various additional features may be added to the devices disclosed herein to confer additional properties to the devices disclosed herein. Examples of such features include, but are not limited to one or more lumens, ability to apply a vacuum or suction to the target anatomy, ability to visualize one or more regions of the target anatomy, ability to limit the depth of insertion into the target anatomy, ability to deploy the antenna, ability to connect to a source of energy, etc.

In any of the embodiments disclosed herein, a medical procedure using working device 104 may be terminated or prevented from starting if the position and/or deployment of working device 104 and/or working element 106 are improper. This may be done by one or more of: preventing energy delivery through working device 104, shutting down a mechanical or electrical function of working device 104, and informing the user about improper position and/or deployment of working device 104 and/or working element 106.

Any of the fluids disclosed herein may be used for a medical function. Examples of such functions include, but are not limited to: cooling or heating an anatomical region or a device, providing a pharmacological function such as disclosed elsewhere in this specification, modifying the performance of the medical procedure, etc.

Several examples or embodiments of the invention have been discussed herein, but various modifications, additions and deletions may be made to those examples and embodiments without departing from the intended spirit and scope of the invention. Thus, any element, component, method step or attribute of one method or device embodiment may be incorporated into or used for another method or device embodiment, unless to do so would render the resulting method or device embodiment unsuitable for its intended use. For example, several embodiments of endoscopic methods may be created by an endoscope 100 of one embodiment with a cannula 102 of another embodiment unless to do so would render the resulting embodiment unsuitable for its intended use. For example, several embodiments of endoscopic methods may be created wherein multiple endoscopes are inserted using cannula 102 unless to do so would render the resulting embodiment unsuitable for its intended use. If the various steps of a method are disclosed in a particular order, the various steps may be carried out in any other order unless doing so would render the method embodiment unsuitable for its intended use. Various reasonable modifications, additions and deletions of the described examples or embodiments are to be considered equivalents of the described examples or embodiments.

We claim:

1. A method of performing a medical procedure within an anatomical region through a tract leading to the anatomical region, the method comprising:
   inserting a device into the tract where the device is configured with an endoscope that permits visualization, the device further including a channel;
   visualizing the tract or the anatomical region using the endoscope;
   navigating the device and endoscope through the tract;
   positioning a distal region of the channel in a target location while using visualization from the endoscope to guide the device to the target location;
   removing the endoscope while maintaining the distal region of the channel at the target location;
   advancing a medical device through the channel to the target location after removing the endoscope from the channel;
   determining at least one treatment parameter of a medical procedure from the step of visualizing the anatomical region using the endoscope, wherein the at least one parameter is an energy dose based on the size of the anatomical region ; and
   performing a medical procedure in the anatomical region by applying energy to the anatomical region with the medical device.

2. The method of claim 1, further comprising performing a visual analysis using the endoscope, where the visual analysis affects the medical procedure.

3. The method of claim 2, where the visual analysis is selected from a group consisting of
   screening a patient for eligibility of the medical procedure;
   checking an anatomical or a pathological landmark; and
   measuring at least one parameter of the anatomical region.

4. The method of claim 3, further comprising performing a second medical procedure using the medical device.

5. The method of claim 3, wherein the endoscope is used to visualize the anatomical region before and after performing the medical procedure, and the method further comprises the step of estimating a change in the anatomical region due to the medical procedure.

6. The method of claim 5, wherein the change in the anatomical region due to the medical procedure is used for one or more of: to determine the necessity of a second medical procedure using the medical device, to confirm the effect of the medical procedure, to estimate the outcome of the medical procedure.

7. The method of claim 1, further comprising the step of introducing the endoscope to the anatomical region using the channel after performing the medical procedure.

8. The method of claim 7, further comprising confirming an effect of the medical procedure using the endoscope.

9. The method of claim 1, further comprising distending the anatomical region using one of: fluid based distension and mechanical distension without a distension fluid.

10. The method of claim 9, wherein the step of distending the anatomical region is used for one or more of: visualizing an interior surface of the anatomical region, visualizing anatomical landmarks of the anatomical region, and flushing the anatomical region.

11. The method of claim 1, further comprising the step of removing one or more materials from the anatomical region through the channel.

12. The method of claim 1, wherein the channel is selected from a group consisting of a sheath and an elongate device comprising a lumen.

13. The method of claim 1, further comprising the step of confirming one or both of: position and deployment of the medical device.

14. The method of claim 13, wherein the step of confirming the deployment of the medical device comprises the step of confirming that an antenna of the medical device is deployed to one of: the greatest transverse dimension, the greatest volume, and the greatest longitudinal dimension that is mechanically possible in the anatomical region.

15. The method of claim 13, wherein the step of confirming the position and/or deployment of the medical device comprises one of: comparing a measured insertion depth of the medical device with an expected insertion depth, measuring a returned power level of microwave energy delivered to the medical device, measuring an inflation volume of a balloon, measuring pressure at a point over or inside the medical device, measuring temperature, measuring a dimension of the medical device, using an imaging modality, checking for perforation, noting the pain or discomfort felt by a patient, feeling a resistance to insertion of the medical device.

16. The method of claim 13, comprising confirming that the distal end of the medical device is touching a distal end of the anatomical region.

17. The method of claim 13, further comprising preventing the start of a medical procedure if one or both of: position and deployment of the medical device are improper.

18. The method of claim 1, further comprising sealing a region between the channel and the tract or the anatomical region.

19. The method of claim 1, further comprising inserting a tube into the channel to stiffen the channel.

20. The method of claim 1, further comprising converting the medical device between an undeployed configuration when introduced using the channel and a deployed configuration inside the anatomical region.

21. The method of claim 1, further comprising folding the medical device to reduce a dimension of the medical device.

22. The method of claim 1, wherein the anatomical region is a uterine cavity, the medical device is an endometrial ablation device, the tract is a uterocervical canal, and the endoscope is one of: a hysteroscope and an intra-uterine ultrasound probe.

23. The method of claim 1, further comprising steering the device to the anatomic region.

24. The method of claim 1, wherein the treatment parameter is selected from the group consisting of: ablation power, ablation time, energy dose, deployed size of a working element, treatment temperature, treatment target, zone of resection, and a cutting site.

* * * * *